(12) United States Patent
Yoshii

(10) Patent No.: US 10,959,796 B2
(45) Date of Patent: Mar. 30, 2021

(54) MEDICAL INSTRUMENT

(71) Applicant: Olympus Corporation, Hachioji (JP)

(72) Inventor: Toshihiro Yoshii, Hirosaki (JP)

(73) Assignee: OLYMPUS CORPORATION, Tokyo (JP)

( * ) Notice: Subject to any disclaimer, the term of this patent is extended or adjusted under 35 U.S.C. 154(b) by 275 days.

(21) Appl. No.: 16/269,104

(22) Filed: Feb. 6, 2019

(65) Prior Publication Data

US 2019/0167368 A1    Jun. 6, 2019

Related U.S. Application Data

(63) Continuation of application No. PCT/JP2016/089112, filed on Dec. 28, 2016.

(51) Int. Cl.
| | |
|---|---|
| *A61B 34/37* | (2016.01) |
| *A61B 17/29* | (2006.01) |
| *B25J 9/10* | (2006.01) |
| *B25J 17/02* | (2006.01) |

(Continued)

(52) U.S. Cl.
CPC .............. *A61B 34/37* (2016.02); *A61B 17/29* (2013.01); *A61B 34/30* (2016.02); *A61B 34/71* (2016.02); *B25J 9/104* (2013.01); *B25J 17/02* (2013.01); *A61B 2034/301* (2016.02); *A61B 2034/305* (2016.02)

(58) Field of Classification Search
CPC ......... A61B 34/30; A61B 17/29; A61B 34/37; A61B 34/71; A61B 2034/301; A61B 2034/305; B25J 9/104; B25J 17/02
See application file for complete search history.

(56) References Cited

U.S. PATENT DOCUMENTS

| | | |
|---|---|---|
| 2004/0199147 A1 | 10/2004 | Nishizawa et al. |
| 2007/0199399 A1 | 8/2007 | Okazaki et al. |
| 2010/0198253 A1 | 8/2010 | Jinno et al. |

(Continued)

FOREIGN PATENT DOCUMENTS

| | | |
|---|---|---|
| JP | 59-232787 | 12/1984 |
| JP | 2004-122286 | 4/2004 |

(Continued)

OTHER PUBLICATIONS

International Search Report and Written Opinion from corresponding International Application No. PCT/JP2016/089112, dated Mar. 21, 2017.

*Primary Examiner* — George J Ulsh
(74) *Attorney, Agent, or Firm* — Scully, Scott, Murphy & Presser, P.C.

(57) ABSTRACT

The disclosed technology is directed to a medical instrument comprises a first pulley configured to be rotatable about a rotational shaft. A transmitting member having a first end portion and a second end portion. The first end portion is disposed along an outer circumferential surface of the first pulley and the second end portion extends tangentially to the first pulley and away from the first pulley. The transmitting member being capable of rotating the first pulley upon being actuated to move forwardly or rearwardly in longitudinal directions thereof. A dislodgement guard is disposed on at least one side of the first pulley along a direction in which the rotational shaft extends with respect to the second end portion of the transmitting member for preventing the transmitting member from being dislodged off the first pulley.

4 Claims, 16 Drawing Sheets

(51) Int. Cl.
  *A61B 34/30* (2016.01)
  *A61B 34/00* (2016.01)

(56) References Cited

U.S. PATENT DOCUMENTS

| | | |
|---|---|---|
| 2016/0317236 A1 | 11/2016 | Hyodo et al. |
| 2017/0135710 A1 | 5/2017 | Hasegawa et al. |

FOREIGN PATENT DOCUMENTS

| | | |
|---|---|---|
| JP | 2006-026797 | 2/2006 |
| JP | 2007-223039 | 9/2007 |
| JP | 2010-178798 | 8/2010 |
| JP | 2011-200593 | 10/2011 |
| JP | 2013-158571 | 8/2013 |
| JP | 5500715 | 3/2014 |
| WO | 2010126129 | 11/2010 |
| WO | 2015111475 | 7/2015 |
| WO | 2016136676 | 9/2016 |

MEDICAL INSTRUMENT

CROSS-REFERENCE TO RELATED APPLICATION

This application is a continuation application of PCT Application No. PCT/JP 2016/089112 filed on Dec. 28, 2016, which is hereby incorporated by reference in its entirety.

TECHNICAL FIELD

The present invention relates to a medical instrument.

DESCRIPTION OF THE RELATED ART

There is a master-slave medical manipulator having a master manipulator operated by a user or an operator and a slave manipulator actuated based on the signals generated by the master manipulator. Such a medical manipulator is equipped with a medical instrument for treating a target area under remote control.

Usually, an end effector for performing various tasks is mounted on the distal end of a medical instrument. The end effector opens and closes its own part such as a gripper having a pair of forceps. There is also a medical instrument that has one or more joints so that the medical instrument can change its direction of an end effector in the body of a patient.

Japanese Patent No. 5500715 discloses a structure having a combination of gears for actuating an end effector. A pulley is mounted on the shaft of one of the gears which is disposed at the rearmost end of the structure. Two wires are wound around the pulley. When the first wire is pulled, a plurality of gears are rotated to open a gripper. When the second wire is pulled, the gears are reversed to close the gripper.

Some medical instruments are used to perform precision treatments in patient's bodies. Such medical instruments are required to operate with high degree of precision. Previous attempts have failed to find a solution to a problem where it is difficult to actuate joints with wires while making attempts to improve the precision of medical instruments.

BRIEF SUMMARY OF EMBODIMENTS

The disclosed technology is directed a medical instrument that is capable of operating with high degree of precision and is prevented from being in situations that are rendered According to the technology disclosed herein, a medical instrument includes a pulley rotatable about a rotational shaft. A transmitting member is slender in shape and has a portion disposed along an outer circumferential surface of the pulley and one end portion extending tangentially to the pulley and away from the pulley. The transmitting member is capable of rotating the pulley upon being actuated to move forwardly or rearwardly in longitudinal directions thereof. A dislodgement guard is disposed on at least one side along a direction in which the rotational shaft extends with respect to the one end portion of the transmitting member, for preventing the transmitting member from being dislodged off the pulley. The one end portion of the transmitting member may be progressively displaced along the direction in which the rotational shaft extends, in a direction away from the pulley.

The medical instrument of the disclosed technology disclosed herein may further include a gear having a pitch circle diameter smaller than the pulley. The gear is disposed coaxially with the pulley on at least one side along a direction in which the rotational shaft extends with respect to the pulley, for rotation in unison with the pulley. The dislodgement guard is disposed to fill at least a portion of a space around the gear. The medical instrument may further include a second pulley disposed coaxially with the pulley with the gear being interposed between the pulley and the second pulley, the dislodgement guard having at least a portion disposed between the pulley and the second pulley. The dislodgement guard may have a guide for defining a direction in which a portion of the transmitting member extends away from the pulley. A first end portion of the transmitting member in the longitudinal directions is attached to an outer circumferential surface of the pulley. In this case, the dislodgement guard may have at least a portion disposed more closely to the second end portion of the transmitting member than the rotational shaft. The medical instrument is capable of operating with high precision and is prevented from causing situations in which it is rendered inoperative.

BRIEF DESCRIPTION OF THE DRAWINGS

The technology disclosed herein, in accordance with one or more various embodiments, is described in detail with reference to the following figures. The drawings are provided for purposes of illustration only and merely depict typical or example embodiments of the disclosed technology. These drawings are provided to facilitate the reader's understanding of the disclosed technology and shall not be considered limiting of the breadth, scope, or applicability thereof. It should be noted that for clarity and ease of illustration these drawings are not necessarily made to scale.

DETAILED DESCRIPTION OF THE EMBODIMENTS

In the following description, various embodiments of the technology will be described. For purposes of explanation, specific configurations and details are set forth in order to provide a thorough understanding of the embodiments. However, it will also be apparent to one skilled in the art that the technology disclosed herein may be practiced without the specific details. Furthermore, well-known features may be omitted or simplified in order not to obscure the embodiment being described.

Figure 1:
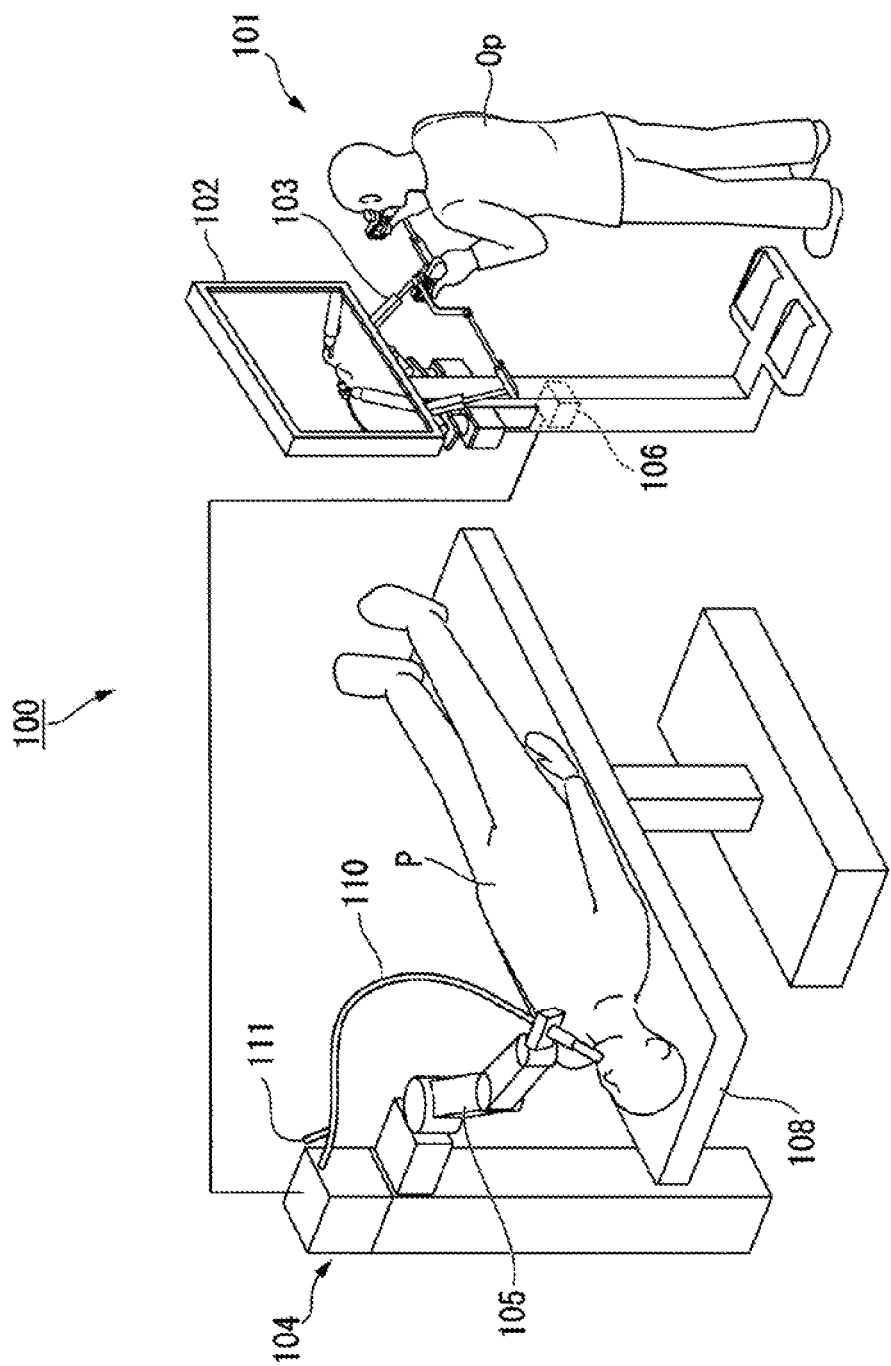
FIG. 1 is an overall view of a medical manipulator used with a medical instrument according to an embodiment of the technology disclosed herein.

FIG. 1 is a perspective view of an overall arrangement of a medical manipulator 100 used with a medical instrument according to the embodiment of the technology disclosed herein. The medical manipulator 100 has a master-slave remote control system. The medical manipulator 100 includes a master manipulator 101, a slave manipulator 104, and a control apparatus 106.

The master manipulator 101 functions as a master for transferring operating movement of an operator (Op) to the slave manipulator 104. The master manipulator 101 includes a display unit 102 such as a liquid crystal display or the like and a master arm 103 gripped and operated by the operator (Op). The master arm 103 has a structure capable of operating about multiple axes. Operations that are performed on the master arm 103 are input to the control apparatus 106.

The control apparatus 106 includes a master controller (not depicted) for accepting inputs from the master manipulator 101 and a slave controller (not depicted) for outputting drive signals to the slave manipulator 104. The master controller generates operation commands for actuating the slave manipulator 104 on the basis of inputs from the master manipulator 101, and outputs the operation commands to the slave controller. The slave controller generates drive signals for actuating the slave manipulator 104 on the basis of operation commands output from the master controller, and outputs the drive signals to the slave manipulator 104.

The slave manipulator 104 is installed near an operating table 108 on which a patient P rests. The slave manipulator 104 has a slave arm 105 that is actuated according to drive signals output from the slave controller. The slave arm 105 has a plurality of joints with multiple degrees of freedom and is capable of operating about multiple axes. The joints with multiple degrees of freedom are individually actuated by power units, which is not depicted. The power units may include electric motors having servo mechanisms (servo motors) each of which including an incremental encoder, a speed reducer, and etc.

The slave manipulator 104 is combined with a soft endoscope 110. The endoscope 110 is supported on the distal end of the slave arm 105 for inserting into the body of the patient P. The endoscope 110 is provided with a channel (not depicted) into which a medical instrument (shown in FIG. 2) can be inserted. The medical instrument according to the present embodiment is inserted into the channel from an insertion opening 111 defined in the proximal end of the endoscope 110, prior to use. The endoscope 110 includes observing means for acquiring images of the body of patient. Images acquired by the observing means are displayed on the display unit 102.

Figure 2:
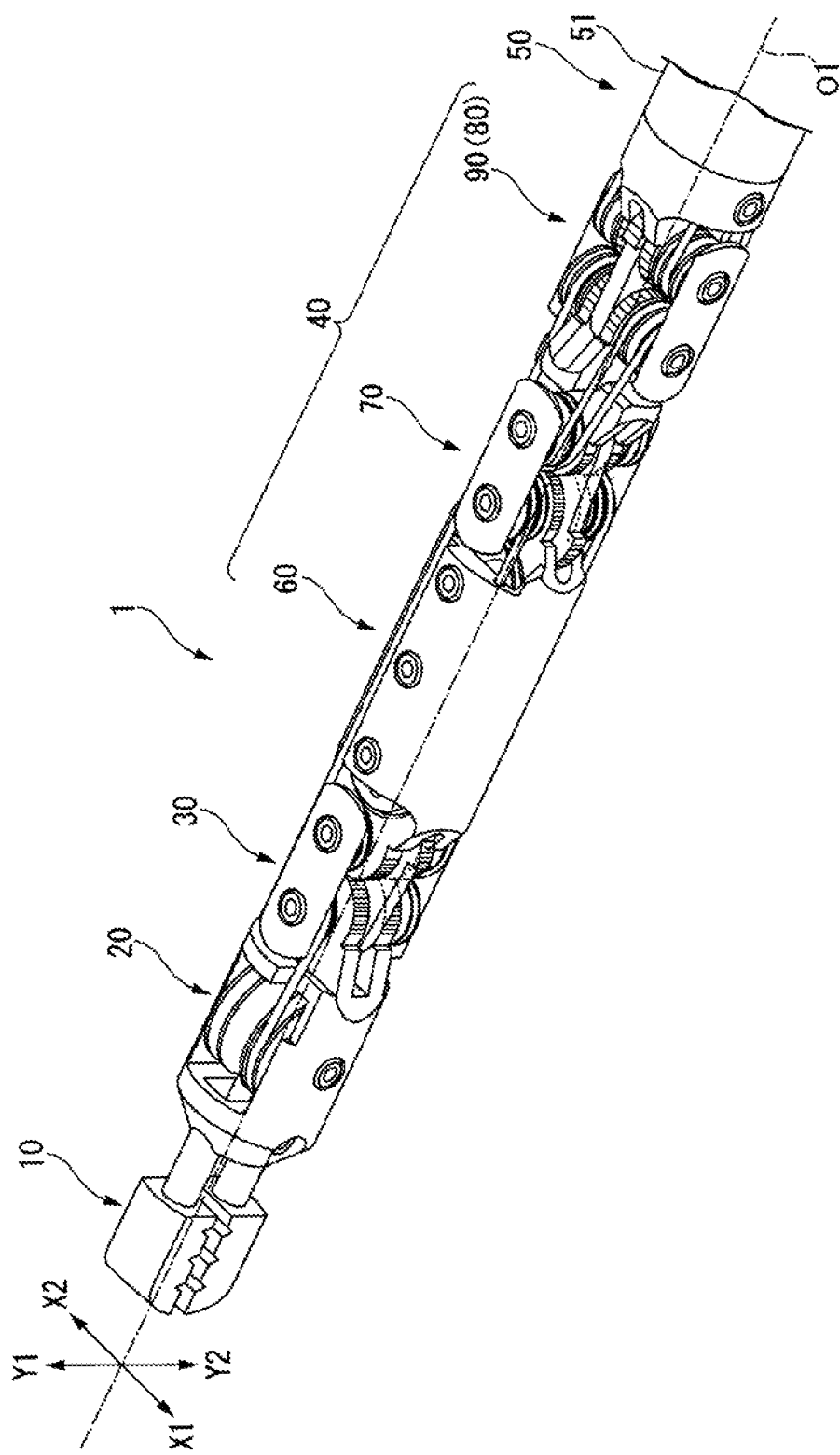
FIG. 2 is a perspective view of a distal end portion of the medical instrument used with the medical manipulator depicted in FIG. 1.

FIG. 2 is a perspective view depicting a distal end portion of the medical instrument 1 used with the medical manipulator 100. The medical instrument 1 is elongated along a longitudinal axis O1 thereof. In the following description, a side of the medical instrument 1 that is closer to a target area to be treated is referred to as "distal-end side" whereas a side of the medical instrument 1 that is opposite to the distal-end side is referred to as a "proximal-end side." Furthermore, an end portion of a member that is closer to the distal-end side is referred to as "distal-end portion," whereas an end portion of the member that is closer to the proximal-end side is referred to as "proximal-end portion." In addition, two intersecting directions that are perpendicular to one another as well as to the longitudinal axis O1 are referred to as an X1 direction and a Y1 direction, and a direction opposite to the X1 direction is referred to as an X2 direction, whereas a direction opposite to the Y1 direction is referred to as a Y2 direction.

As depicted in FIG. 2, the medical instrument 1 includes an end effector 10, a distal-end arm 20 connected to the end effector 10. A distal-end joint 30 is connected to a proximal-end side of the distal-end arm 20. An intermediate arm 40 is connected to a proximal-end side of the distal-end joint 30, and a main body 50 is connected to a proximal-end side of the intermediate arm 40. The intermediate arm 40 has an arm 60 connected to the distal-end joint 30, an intermediate joint 70 connected to a proximal-end side of the arm 60, and an arm 80 connected to a proximal-end side of the intermediate arm 70 and the main body 50. The arm 80 has a proximal-end joint 90. In the medical instrument 1, the end effector 10, the distal-end arm 20, the distal-end joint 30, the arm 60, the intermediate joint 70, the proximal-end joint 90 (the arm 80), and the main body 50 are successively arranged along the longitudinal axis O1 from the distal-end side toward the proximal-end side. The distal-end joint 30, the intermediate joint 70, the proximal-end joint 90 are bendable independently of one another.

Figure 3:
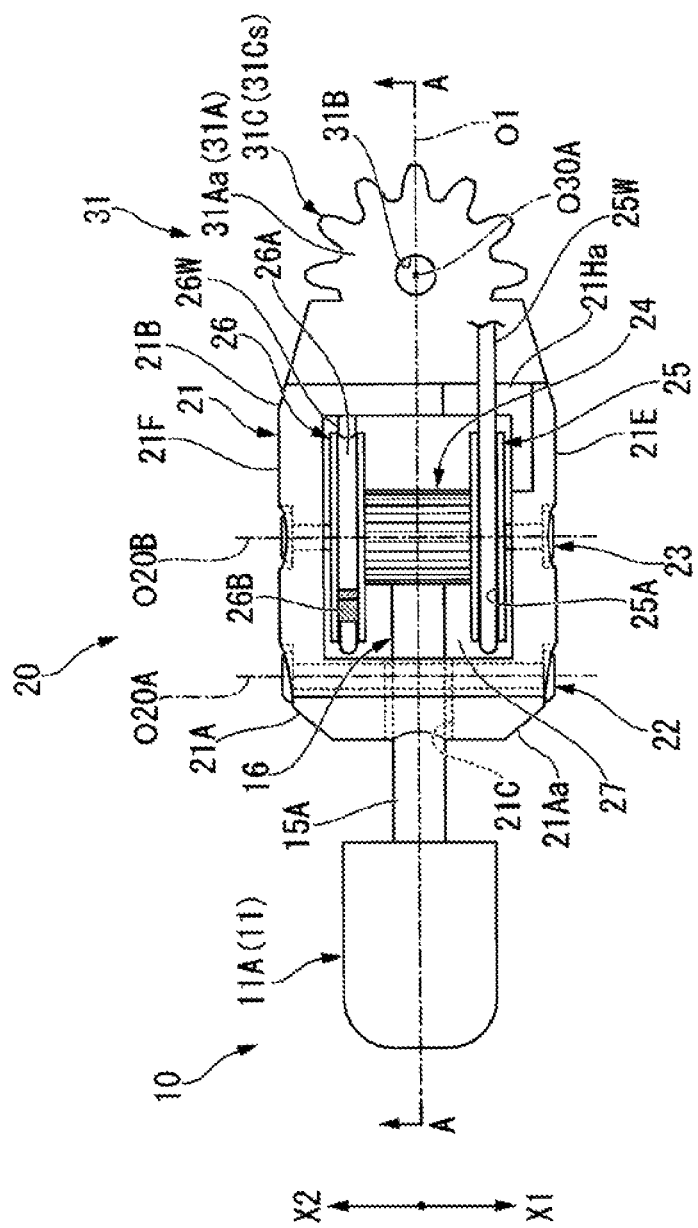
FIG. 3 is a plan view of the structure of an end effector of the medical instrument depicted in FIG. 1.
Figure 4:
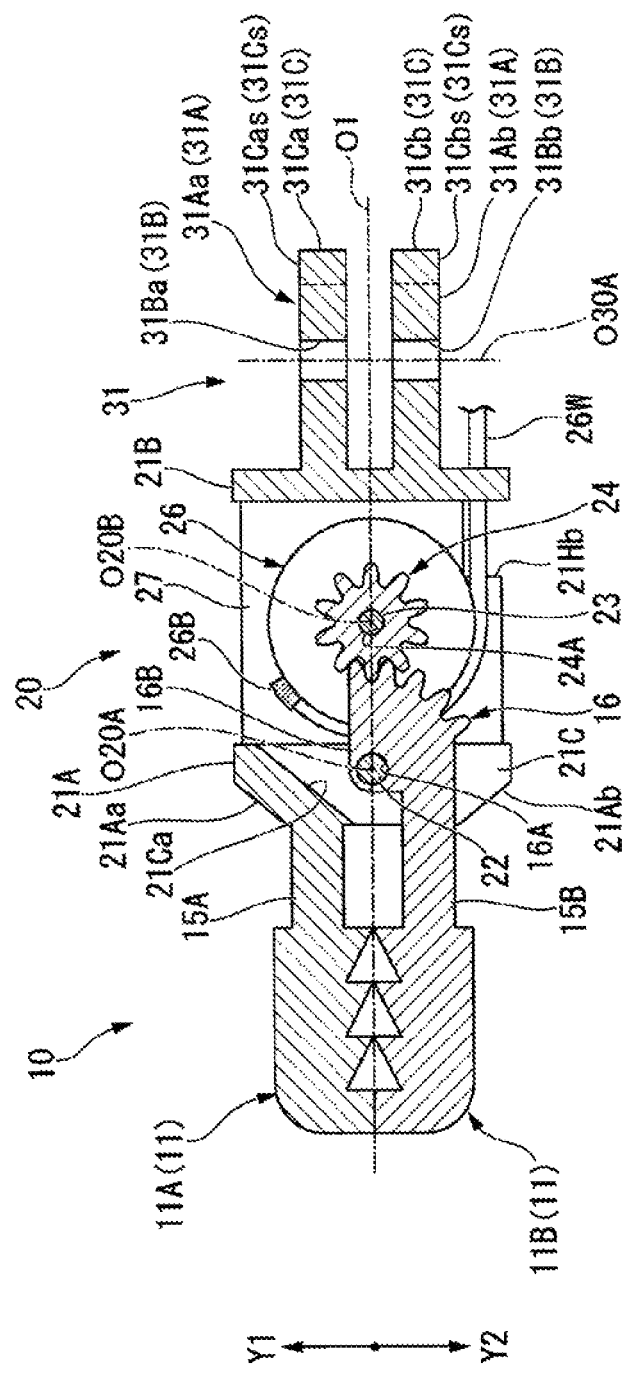
FIG. 4 is a cross-sectional view taken along line A-A of FIG. 3.

FIG. 3 is a plan view of the structure of the end effector 10 and the distal-end arm 20 and FIG. 4 is a cross-sectional view taken along line A-A of FIG. 3. The present embodiment illustrates an example in which the medical instrument 1 defines as gripping forceps. The end effector 10 includes a pair of openable and closeable grippers 11 including a first gripper 11A and a second gripper 11B. A connector 15A is provided on a proximal-end side of the first gripper 11A. The first gripper 11A is attached to the distal-end arm 20 by the connector 15A. A connector 15B is provided on a proximal-end side of the second gripper 11B. A gear 16 is provided on a proximal-end portion of the connector 15B. The gear 16 is angularly movable and mounted on a turn shaft 22. The turn shaft 22 is disposed in the distal-end arm 20 and extends in the X1 direction in engagement with the distal-end arm 20. The gear 16 has a circular hole 16A defined therein around an axis O20A perpendicular to the longitudinal axis O1 and parallel to the X1 direction and extending in the X1 direction through the gear 16. The turn shaft 22 is inserted through the circular hole 16A. The turn shaft 22 is a cylindrical in shape with the axis O20A defining as its central axis and extends in the X1 direction. Both ends of the turn shaft 22 are supported on a distal-end portion 21A of a main body 21. The turn shaft 22 is supported by the gear 16 for relative angular movement about the axis O20A through the circular hole 16A. In other words, the gear 16 in which the second gripper 11B is connected thereto are both angularly movable about the axis O20A with respect to the turn shaft 22. The pair of grippers 11 is configured to be opened or closed in the respective Y1 and Y2 directions as the second gripper 11B is angularly moved with respect to the first gripper 11A. The gear 16 has a sectorial region about the axis O20A at its center more closely to the proximal-end side than the circular hole 16A, with teeth formed on the arc of the sectorial region. The gear 16 is held in mesh with a gear 24 on the distal-end arm 20.

The distal-end arm 20 has the main body 21, the gear 24, a pulley 25, and a pulley 26. The main body 21 is of a substantially cylindrical outer profile with the longitudinal axis O1 defining as its central axis. A housing space 27 that extends through the main body 21 in the Y1 direction is defined between the distal-end portion 21A of the main body 21 and a proximal-end portion 21B thereof. The distal-end portion 21A has a portion 21Aa extending in the Y1 direction and to which the connector 15A of the first gripper 11A is attached. The distal-end portion 21A has a portion 21Ab that extends in the Y2 direction and has a recess 21C defined therein. The recess 21C extends through the distal-end portion 21A in a direction along the longitudinal axis O1, and is in communication with the housing space 27. The recess 21C is open in the Y2 direction and extends in the Y1 direction beyond the axis O20A. The recess 21C has an end face 21Ca in the Y1 direction which is oriented toward the Y1 direction from the distal-end side toward the proximal-end side. The end face 21Ca is angled with respect to the longitudinal axis O1. The end face 21Ca limits the range of angular movement of the second gripper 11B by abutting against a side face 16B of the gear 16 which faces in the Y1 direction. The dimension of the recess 21C along the X1 direction is larger than the dimension along the X1 direction of the connector 15B of the second gripper 11B and the gear 16. The distal-end portion 21A has through holes defined in both sides thereof spaced across the recess 21C along the X1 direction, with the axis O20A defining as their central axes. The turn shaft 22 has both ends angularly movable that is supported in these through holes.

The housing space 27 is of a rectangular shape with respect to the Y1 direction. The gear 24, the pulley 25, the pulley 26, and the gear 16 of the second gripper 11B are interconnected and disposed in the housing space 27. The main body 21 includes a side portion 21E defining as a side wall of the housing space 27 in the X1 direction and having a through hole defined therein whose central axis is given as an axis O20B perpendicular to the longitudinal axis O1 and parallel to the X1 direction. The main body 21 also includes a side portion 21F defining as a side wall of the housing space 27 in the X2 direction and having a through hole defined therein whose central axis is given as the axis O20B. A cylindrical turn shaft 23, with the axis O20B defining as its central axis and extends in the X1 direction, has both ends inserted and angularly movably each supported in the through hole in the side portion 21E and the through hole in the side portion 21F. In other words, the main body 21 includes respective first and second side portions (walls) 21E and 21F which form the housing space 27. The respective first and second walls 21E and 21F includes a circular hole each of which extends through the thickness of first and second walls and are constructed to receive a cylindrical turn shaft 23.

The gear 24 has a circular hole 24A defined therein around an axis O20B at its center and extending in the X1 direction through the gear 24. The turn shaft 23 is inserted through the circular hole 24A for relative angular movement about the axis O20B. The gear 24 is of a cylindrical shape with the axis O20B at its center. The gear 24 has an outer circumferential surface extending around the axis O20B and having teeth formed thereon. Since the gear 24 is held in mesh with the gear 16 of the second gripper 11B, angular movement of the gear 24 about the axis O20B causes the second gripper 11B to turn about the axis O20A.

The pulley 25 is shaped as a circular plate with the axis O20B defining as its central axis and has a circular hole (not depicted) defined therein which extends in the X1 direction through the pulley 25 with the axis O20B at its center. The pulley 25 has a pulley groove 25A defined in an outer circumferential surface thereof around the axis O20B. The pulley 26 is of the same structure as the pulley 25 and will not described herein to avoid redundancy. The turn shaft 23 is inserted through the circular hole in the pulley 25 and the circular hole in the pulley 26 for relative angular movement about the axis O20B. The pulley 25 is disposed adjacent to the gear 24 in the X1 direction and fixed to the gear 24 for angular movement in unison with the gear 24. The pulley 26 is disposed adjacent to the gear 24 in the X2 direction and fixed to the gear 24 for angular movement in unison with the gear 24.

An operating wire 25W is wound in the pulley groove 25A of the pulley 25. The operating wire 25W has one end fastened to the pulley groove 25A by a fastener (not depicted). The other end of the operating wire 25W is connected to a power transmitter (not depicted) provided on the proximal-end side of the medical instrument 1. The operating wire 25W is wound in the pulley groove 25A counterclockwise as viewed from the X2 direction from the other end toward one end of the operating wire 25W. An operating wire 26W is wound in the pulley groove 26A of the pulley 26. The operating wire 26W has one end fastened to the pulley groove 26A by a fastener 26B. The other end of the operating wire 26W is connected to the power transmitter. The operating wire 26W is wound clockwise in the pulley groove 26A as viewed from the X2 direction from the other end toward one end of the operating wire 26W.

With the above structure, when the operating wire 25W is pulled toward the proximal-end side, the pulley 25 and the gear 24 are turned clockwise as viewed from the X2 direction. The angular movement of the gear 24 causes the gear 16 in mesh with the gear 24 to turn counterclockwise as viewed from the X2 direction in unison with the second gripper 11B. The respective grippers 11A and 11B are now opened. When the operating wire 26W is pulled toward the proximal-end side, the pulley 26 and the gear 24 are turned counterclockwise as viewed from the X2 direction. The angular movement of the gear 24 causes the gear 16 in mesh with the gear 24 to turn clockwise as viewed from the X2 direction in unison with the second gripper 11B. The respective grippers 11A and 11B are now closed. In this position, the respective grippers 11A and 11B are opened and closed with respect to one another by operating the operating wire 25W and the operating wire 26W.

The proximal-end portion 21B of the main body 21 has a recess 21Ha and a recess 21Hb defined therein respectively in which the operating wire 25W and the operating wire 26W extend therethrough. The recess 21Ha is defined in a portion of the proximal-end portion 21B in the X1 direction at an end thereof in the Y1 direction. The operating wire 25W extends through the recess 21Ha. The recess 21Hb is defined in a portion of the proximal-end portion 21B in the X2 direction at an end thereof in the Y2 direction. The operating wire 26W extends through the recess 21Hb.

Figure 5:
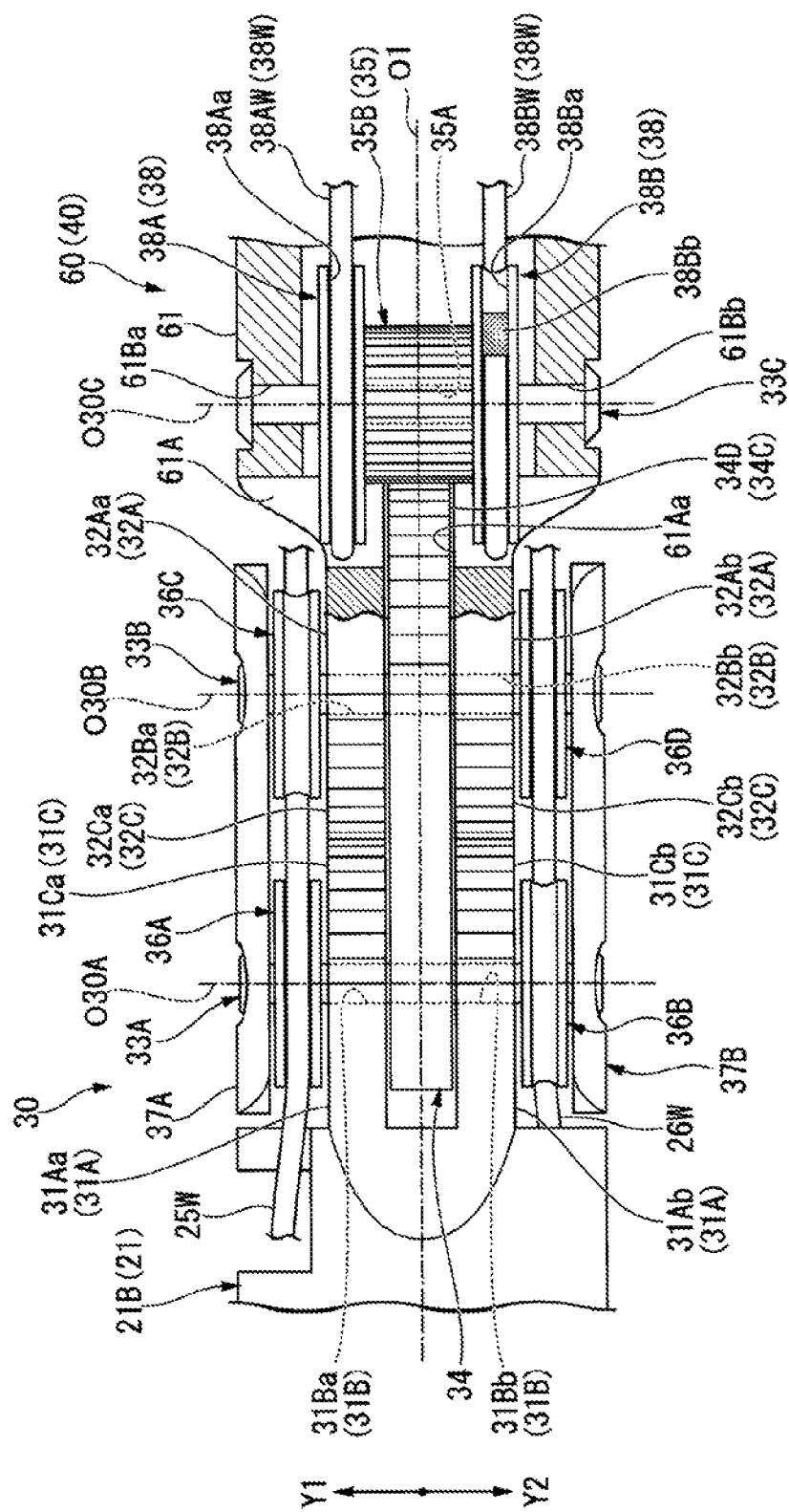
FIG. 5 is a view, partly in cross section, depicting the structure of a distal-end joint of the medical instrument.
Figure 6:
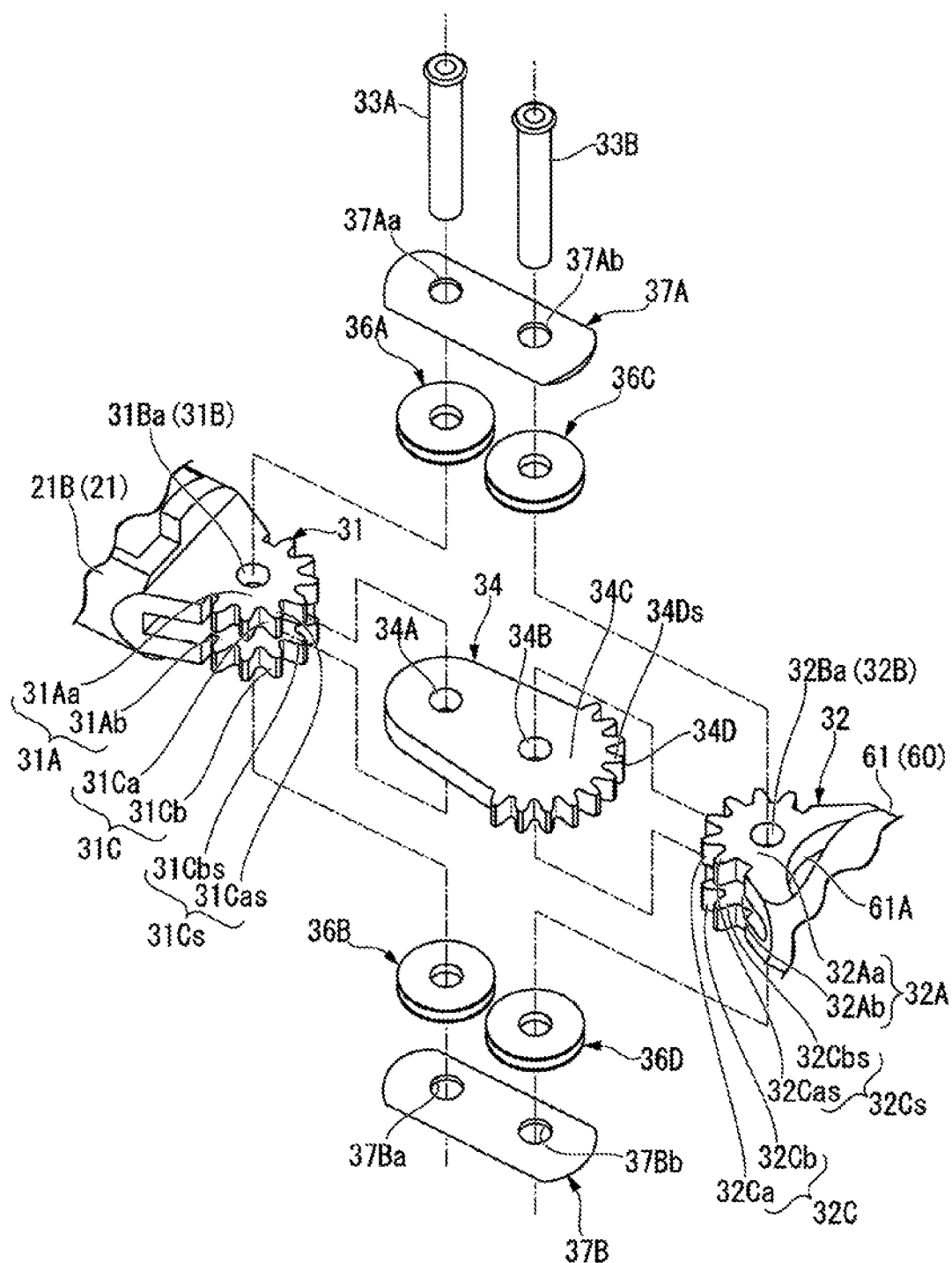
FIG. 6 is an exploded perspective view of the distal-end joint of the medical instrument depicted in FIG. 1.
Figure 7:
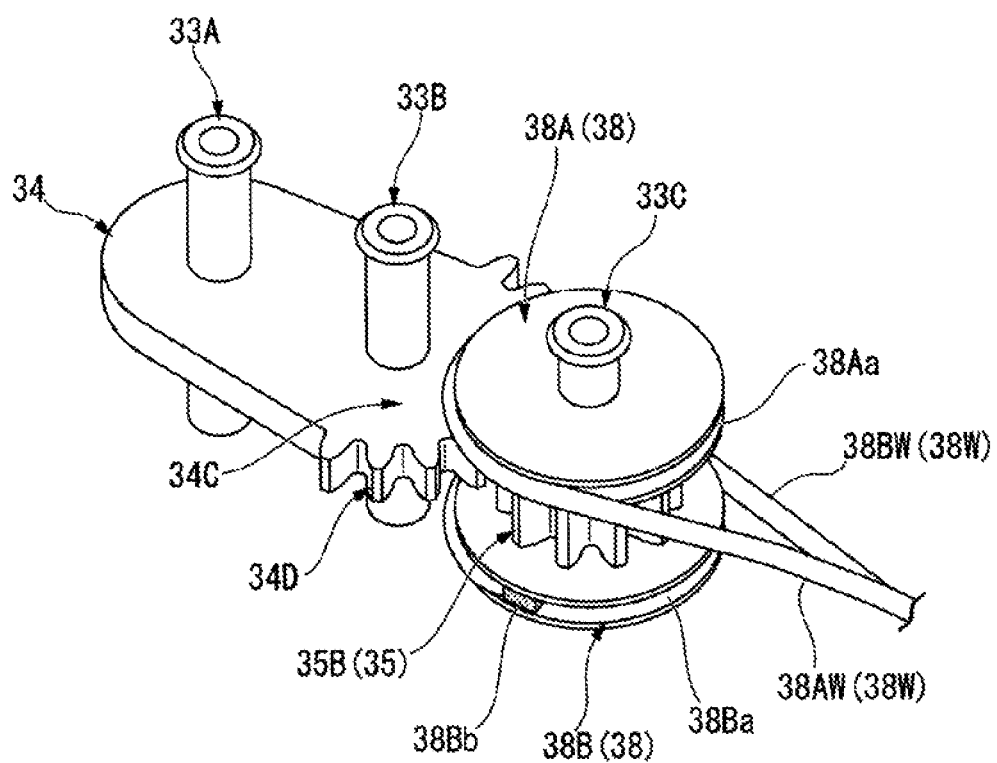
FIG. 7 is a perspective view of the structure of an intermediate connector and a rotation transmitter of the distal-end joint.

FIG. 5 is a view, partly in cross section, depicting the structure of the distal-end joint 30 of the medical instrument 1. FIG. 6 is an exploded perspective view of the distal-end joint 30. FIG. 7 is a perspective view of the structure of an intermediate connector 34 and a rotation transmitter 35 of the distal-end joint 30. The distal-end joint 30 includes a double joint that is bendable about the Y1 direction. The distal-end joint 30 has an axis O30A, an axis O30B, and an axis O30C. The axis O30B is spaced from the axis O30A and extends parallel to the axis O30A. The axis O30B is disposed more closely to the proximal-end side than the axis O30A. The axis O30C is spaced from the axis O30A and the axis O30B and extends parallel to the axis O30A and the axis O30B. The axis O30C is disposed more closely to the proximal-end side than the axis O30B and is fixed in position with respect to the axis O30B. According to the present embodiment, the axis O30A, the axis O30B, and the axis O30C are perpendicular to the longitudinal axis O1 and parallel to the Y1 direction.

The distal-end joint 30 has a distal-end connector 31, a proximal-end connector 32, the intermediate connector 34, and the rotation transmitter 35 all of which are attached to one another as will be described hereinafter.

The distal-end connector 31 is attached to a proximal-end side of the proximal-end portion 21B of the main body 21. The distal-end connector 31 has a rotation transmitter 31A provided on a proximal-end side thereof. The rotation transmitter 31A is angularly movable about the axis O30A. The rotation transmitter 31A has a circular hole 31B defined therein which extends in the Y1 direction therethrough with the axis O30A at its center. A cylindrical turn shaft 33A, with the axis O30A defining as its central axis, extends in the Y1 direction and is inserted through the circular hole 31B. The cylindrical turn shaft 33A is supported by the rotation transmitter 31A for relative angular movement about the axis O30A through the circular hole 31B. In other words, the rotation transmitter 31A is angularly movable about the axis O30A with respect to the turn shaft 33A.

The rotation transmitter 31A is divided into an upper rotation transmitter 31Aa and a lower rotation transmitter 31Ab in a direction along the axis O30A, i.e., in the Y1 direction or the Y2 direction. The upper rotation transmitter 31Aa and the lower rotation transmitter 31Ab are spaced apart from each other in the Y1 direction and disposed parallel to each other with the longitudinal axis O1 interposed therebetween. The upper rotation transmitter 31Aa is disposed on one side of the longitudinal axis O1 in the Y1 direction, and the lower rotation transmitter 31Ab is disposed on the other side of the longitudinal axis O1 in the Y2 direction. The upper rotation transmitter 31Aa has a circular hole 31Ba defined therein as part of the circular hole 31B, which extends in the Y1 direction therethrough with the axis O30A at its center. The lower rotation transmitter 31Ab has a circular hole 31Bb defined therein as part of the circular hole 31B, which extends in the Y1 direction therethrough with the axis O30A at its center. The turn shaft 33A is inserted through the circular hole 31Ba and the circular hole 31Bb.

The rotation transmitter 31A has a gear 31C including a sectorial region 31Cs about the axis O30A at its center and teeth formed on the arc of the sectorial region 31Cs. The upper rotation transmitter 31Aa has an upper gear 31Ca, as part of the gear 31C, including a sectorial region 31Cas about the axis O30A at its center and teeth formed on the arc of the sectorial region 31Cas. The lower rotation transmitter 31Ab has a lower gear 31Cb, as part of the gear 31C, including a sectorial region 31Cbs about the axis O30A at its center and teeth formed on the arc of the sectorial region 31Cbs. The gear 31C is held in mesh with a gear 32C of a rotation transmitter 32A to be described hereinafter. Specifically, the upper gear 31Ca is held in mesh with an upper gear 32Ca of the gear 32C, whereas the lower gear 31Cb is held in mesh with a lower gear 32Cb of the gear 32C. The rotation transmitter 31A and the rotation transmitter 32A are thus operatively connected to each other such that they are angularly movable in combined relationship with respect to one another.

The proximal-end connector 32 is provided on a distal-end side of the intermediate arm 40 and is attached to the intermediate arm 40. According to the present embodiment, the proximal-end connector 32 is attached to a distal-end portion 61 of the arm 60 of the intermediate arm 40. The proximal-end connector 32 has the rotation transmitter 32A provided on a distal-end side thereof. The rotation transmitter 32A is angularly movable about the axis O30B. Specifically, as is the case with the rotation transmitter 31A, the rotation transmitter 32A has a circular hole 32B defined therein which extends in the Y1 direction therethrough with the axis O30B at its center. A cylindrical turn shaft 33B extends in the Y1 direction with the axis O30B defining as its central axis and is inserted through the circular hole 32B and is supported for angular movement with respect to the rotation transmitter 32A.

The rotation transmitter 32A is divided into an upper rotation transmitter 32Aa and a lower rotation transmitter 32Ab in a direction along the axis O30B, i.e., in the Y1 direction or the Y2 direction. The upper rotation transmitter 32Aa and the lower rotation transmitter 32Ab are disposed in a manner similar to the upper rotation transmitter 31Aa and the lower rotation transmitter 31Ab as described hereinbefore. The upper rotation transmitter 32Aa has a circular hole 32Ba defined therein as part of the circular hole 32B, and the lower rotation transmitter 32Ab has a circular hole 32Bb defined therein as part of the circular hole 32B.

The rotation transmitter 32A has a gear 32C including a sectorial region 32Cs about the axis O30B at its center and teeth formed on the arc of the sectorial region 32Cs. The upper rotation transmitter 32Aa has an upper gear 32Ca as part of the gear 32C, and the lower rotation transmitter 32Ab has a lower gear 32Cb as part of the gear 32C. The upper gear 32Ca has a sectorial region 32Cas as part of the sectorial region 32Cs, and the lower gear 32Cb has a sectorial region 32Cbs as part of the sectorial region 32Cs.

According to the present embodiment, the pitch circle diameter of the gear 31C (the upper gear 31Ca and the lower gear 31Cb) is the same as the pitch circle diameter of the gear 32C (the upper gear 32Ca and the lower gear 32Cb). The dimension of the gear 31C in the Y1 direction is the same as the dimension of the gear 32C in the Y1 direction. In other words, the dimension of the upper gear 31Ca in the Y1 direction and the dimension of the upper gear 32Ca in the Y1 direction are equal to one another, and the dimension of the lower gear 31Cb in the Y1 direction and the dimension of the lower gear 32Cb in the Y1 direction are equal to one another.

The intermediate connector 34 is angularly movable about the axis O30A and is also angularly movable about the axis O30B. According to the present embodiment, the intermediate connector 34 includes a plate-like member which is of substantially an oblong shape as viewed from the Y1 direction. The intermediate connector 34 has a circular hole 34A defined in a distal-end side thereof, which extends in the Y1 direction therethrough with the axis O30A at its center. The turn shaft 33A is inserted through the circular hole 34A. The turn shaft 33A is supported by the intermediate connector 34 for relative angular movement about the axis O30A through the circular hole 34A. In other words, the intermediate connector 34 is angularly movable about the axis O30A with respect to the turn shaft 33A. The intermediate connector 34 has a circular hole 34B defined in a proximal-end side thereof, which extends in the Y1 direction therethrough with the axis O30B at its center. The turn shaft 33B is inserted through the circular hole 34B. The turn shaft 33B is supported by the intermediate connector 34 for relative angular movement about the axis O30B through the circular hole 34B. In other words, the intermediate connector 34 is angularly movable about the axis O30B with respect to the turn shaft 33B.

According to the present embodiment, the distal-end side of the intermediate connector 34 is disposed between the upper rotation transmitter 31Aa and the lower rotation transmitter 31Ab of the rotation transmitter 31A. The proximal-end side of the intermediate connector 34 is disposed between the upper rotation transmitter 32Aa and the lower rotation transmitter 32Ab of the rotation transmitter 32A. The intermediate connector 34 is thus disposed with the longitudinal axis O1 included therein. The dimension of the intermediate connector 34 in the Y1 direction is smaller than the dimension between the upper rotation transmitter 31Aa and the lower rotation transmitter 31Ab and the dimension between the upper rotation transmitter 32Aa and the lower rotation transmitter 32Ab.

The intermediate connector 34 has a rotation transmitter 34C provided on a proximal-end portion (end portion) thereof. The rotation transmitter 34C is operatively connected to the rotation transmitter 35 such that the rotation transmitter 34C is angularly moved about the axis O30B in combined relationship to the rotation transmitter 35. According to the present embodiment, the rotation transmitter 34C has a gear 34D including a sectorial region 34Ds about the axis O30B at its center and teeth formed on the arc of the sectorial region 34Ds. The gear 34D is held in mesh with a gear 35B of the rotation transmitter 35 to be described hereinafter. Therefore, angular movement of the rotation transmitter 35 is transmitted through the gear 35B and the gear 34D to the rotation transmitter 34C. The rotation transmitter 34C is thus angularly movable about the axis O30B in combined relationship to the rotation transmitter 35.

A pulley 36A and a pulley 36B are configured on both sides of the rotation transmitter 31A in the Y1 direction. The pulley 36A is a circular plate with the axis O30A defining as its central axis, and has a circular hole defined therein which extends in the Y1 direction therethrough with the axis O30A at its center. The pulley 36A has a pulley groove defined in an outer circumferential surface thereof around the axis O30A. The pulley 36B is of the same structure as the pulley 36A. The turn shaft 33A is inserted through the circular hole in the pulley 36A and the circular hole in the pulley 36B for relative angular movement about the axis O30A. The pulley 36A is disposed on one side of the upper rotation transmitter 31Aa in the Y1 direction, whereas the pulley 36B is disposed on one side of the lower rotation transmitter 31Ab in the Y2 direction. Therefore, the rotation transmitter 31A is disposed between the pulley 36A and the pulley 36B in the Y1 direction. The operating wire 25W extending from the pulley 25 is wound in the pulley groove of the pulley 36A. The operating wire 26W extending from the pulley 26 is wound in the pulley groove of the pulley 36B. A pulley 36C and a pulley 36D are configured on both sides of the rotation transmitter 32A which face in the Y1 direction. The pulley 36C and the pulley 36D are of the same structure as the pulley 36A except that they have the axis O30B, rather than the axis O30A, as their central axis.

The turn shaft 33B is inserted through the circular hole in the pulley 36C and the circular hole in the pulley 36D for relative angular movement about the axis O30B. The pulley 36C is disposed on one side of the upper rotation transmitter 32Aa in the Y1 direction, whereas the pulley 36D is disposed on one side of the lower rotation transmitter 32Ab in the Y2 direction. Therefore, the rotation transmitter 32A is disposed between the pulley 36C and the pulley 36D in the Y1 direction. The operating wire 25W extending from the pulley 36A is wound in the pulley groove of the pulley 36C. The operating wire 26W extending from the pulley 36B is wound in the pulley groove of the pulley 36D.

The pulley 36A and the pulley 36C are disposed in the same position as each other in the Y1 direction. Similarly, the pulley 36B and the pulley 36D are disposed in the same position in the Y1 direction. The operating wire 25W is wound around the pulley 36A from the X1 direction and around the pulley 36C in the X2 direction such that the operating wire 25W crosses the longitudinal direction O1 between the pulley 36A and the pulley 36C as viewed from the Y2 direction. The operating wire 26W is wound around the pulley 36B from the X2 direction and around the pulley 36D in the X1 direction such that the operating wire 26W crosses the longitudinal direction O1 between the pulley 36B and the pulley 36D as viewed from the Y2 direction.

A support member 37A is provided on the sides of the pulley 36A and the pulley 36C which points in the Y1 direction. The support member 37A includes a plate-like member which is of substantially an oblong shape as viewed from the Y1 direction. The support member 37A has a circular hole 37Aa defined therein which extends in the Y1 direction therethrough with the axis O30A at its center. In addition, the support member 37A has a circular hole 37Ab defined therein which extends in the Y1 direction therethrough with the axis O30B at its center. The turn shaft 33A is inserted through the circular hole 37Aa for relative angular movement about the axis O30A. The turn shaft 33B is inserted through the circular hole 37Ab for relative angular movement about the axis O30B.

A support member 37B is provided on the sides of the pulley 36B and the pulley 36D which points in the Y2 direction. The support member 37B is of the same structure as the support member 37A. The turn shaft 33A is inserted through the circular hole 37Ba in the support member 37B for relative angular movement about the axis O30A. The turn shaft 33B is inserted through the circular hole 37Bb in the support member 37B for relative angular movement about the axis O30B.

The turn shaft 33A has both ends each of which is supported by the respective support members 37A and 37B through the respective circular holes 37Aa and 37Ba. Likewise, the turn shaft 33B has both ends each of which is supported by the respective support members 37A and 37B through the respective circular holes 37Ab and the 37Bb.

With the above structure, the turn shaft 33A interconnects the support member 37A, the pulley 36A, the rotation transmitter 31A (e.g., the upper rotation transmitter 31Aa and the lower rotation transmitter 31Ab), the intermediate connector 34, the pulley 36B, and the support member 37B for relative angular movement about the axis O30A. Similarly, the turn shaft 33B interconnects the support member 37B, the pulley 36C, the rotation transmitter 32A (e.g., the upper rotation transmitter 32Aa and the lower rotation transmitter 32Ab), the intermediate connector 34, the pulley 36D, and the support member 37B for relative angular movement about the axis O30B. The distance between the axis O30A and the axis O30B is kept constant by the support member 37A, the intermediate connector 34, and the support member 37B.

The rotation transmitter 35 is angularly movable about the axis O30C. Specifically, the rotation transmitter 35 has a circular hole 35A defined therein which extends in the Y1 direction therethrough with the axis O30C at its center. A cylindrical turn shaft 33C with the axis O30C defining as its central axis and extends in the Y1 direction, is inserted through the circular hole 35A. The turn shaft 33C is supported by the rotation transmitter 35 for relative angular movement about the axis O30C through the circular hole 35A. In other words, the rotation transmitter 35 is angularly movable about the axis O30C with respect to the turn shaft 33C. The rotation transmitter 35 is of a cylindrical shape with the axis O30C at its center and has a gear 35B having teeth formed on an outer circumferential surface thereof around the axis O30C. As noted hereinbefore, the gear 35B is held in mesh with the gear 34D. The pitch circle diameter of the gear 35B is smaller than the pitch circle diameter of the gear 34D. Therefore, the rotating speed of the gear 34D is smaller than the rotating speed of the gear 35B, and the torque of the gear 34D is larger than the torque of the gear 35B.

The distal-end joint 30 also has a pulley 38 angularly movable about the axis O30C and an operating wire 38W wound around the pulley 38. The pulley 38 is connected to the gear 35B for angular movement in unison therewith. According to the present embodiment, the pulley 38 includes a pulley 38A and a pulley 38B, and the operating wire 38W includes an operating wire 38AW and an operating wire 38BW. The pulley 38A is a circular plate in shape with the axis O30C defining as its central axis and has a circular hole (not depicted) defined therein which extends in the Y1 direction therethrough with the axis O30C at its center. The pulley 38A has a pulley groove 38Aa defined in an outer circumferential surface thereof around the axis O30C. The pulley 38B is of the same structure as the pulley 38A and will not be described to avoid redundancy. The turn shaft 33C is inserted through the circular hole in the pulley 38A and the circular hole in the pulley 38B for relative angular movement about the axis O30C. The pulley 38A is disposed adjacent to the gear 35B in the Y1 direction and fixed to the gear 35B for angular movement in unison with the gear 35B. The pulley 38B is disposed adjacent to the gear 35B in the Y2 direction and fixed to the gear 35B for angular movement in unison with the gear 35B.

The operating wire 38AW is wound in the pulley groove 38Aa of the pulley 38A. The operating wire 38AW has one end fastened to the pulley groove 38Aa by a fastener 38Ab as seen best in FIG. 8. The other end of the operating wire 38AW is connected to the power transmitter provided on the proximal-end side of the medical instrument 1. The operating wire 38AW is wound in the pulley groove 38Aa counterclockwise as viewed from the Y2 direction from the other end toward one end of the operating wire 38AW. The operating wire 38BW is wound in the pulley groove 38Ba of the pulley 38B. The operating wire 38BW has one end fastened to the pulley groove 38Ba by a fastener 38Bb. The other end of the operating wire 38BW is connected to the power transmitter provided on the proximal-end side of the medical instrument 1. The operating wire 38BW is wound in the pulley groove 38Ba clockwise as viewed from the Y2 direction from the other end toward one end of the operating wire 38BW. With the above structure, when the operating wire 38AW is pulled toward the proximal-end side, the pulley 38A and the gear 35B are turned counterclockwise as viewed from the Y2 direction. When the operating wire 38BW is pulled toward the proximal-end side, the pulley 38BW and the gear 35B are turned clockwise as viewed from the Y2 direction.

According to the present embodiment, the outside diameter of the pulley 38A and the pulley 38B is larger than the pitch circle diameter of the gear 35B. Consequently, the tension of the operating wire 38AW and the operating wire 38BW which is required to turn the gear 35B is reduced. In addition, a speed reduction occurs between the pulley 38 and the gear 35B. The arm 60 is of a hollow cylindrical shape with the longitudinal axis O1 defining as its central axis. The arm 60 has a housing space 61A defined in a distal-end portion 61 thereof and extending along the longitudinal axis O1. The housing space 61A is disposed in a proximal-end side of the proximal-end connector 32 fixed to the distal-end portion 61. The housing space 61A is held in communication with a space defined between the upper rotation transmitter 32Aa and the lower rotation transmitter 32Ab of the rotation transmitter 32A, in a direction along the longitudinal axis O1 through an opening 61Aa. The distal-end portion 61 has a circular hole 61Ba and a circular hole 61Bb defined therein which extend therethrough with the axis O30C at their centers. The circular hole 61Ba and the circular hole 61Bb are held in communication with the housing space 61A and disposed with the housing space 61A interposed therebetween. The rotation transmitter 35, the pulley 38A, and the pulley 38B are disposed in the housing space 61A. The gear 34D of the rotation transmitter 34C is disposed in the housing space 61A through the opening 61Aa and held in mesh with the gear 35B of the rotation transmitter 35. The turn shaft 33C has both ends each of which is supported in the respective circular holes 61Ba and 61Bb for relative angular movement about the axis O30C. The turn shaft 33C is supported on the distal-end portion 61 through the respective circular hole 61Ba and 61Bb, and the turn shaft 33B is supported on the rotation transmitter 32A of the proximal-end connector 32 attached to the distal-end portion 61. Therefore, the axis O30C is fixed in position with respect to the axis O30B.

Figure 8:
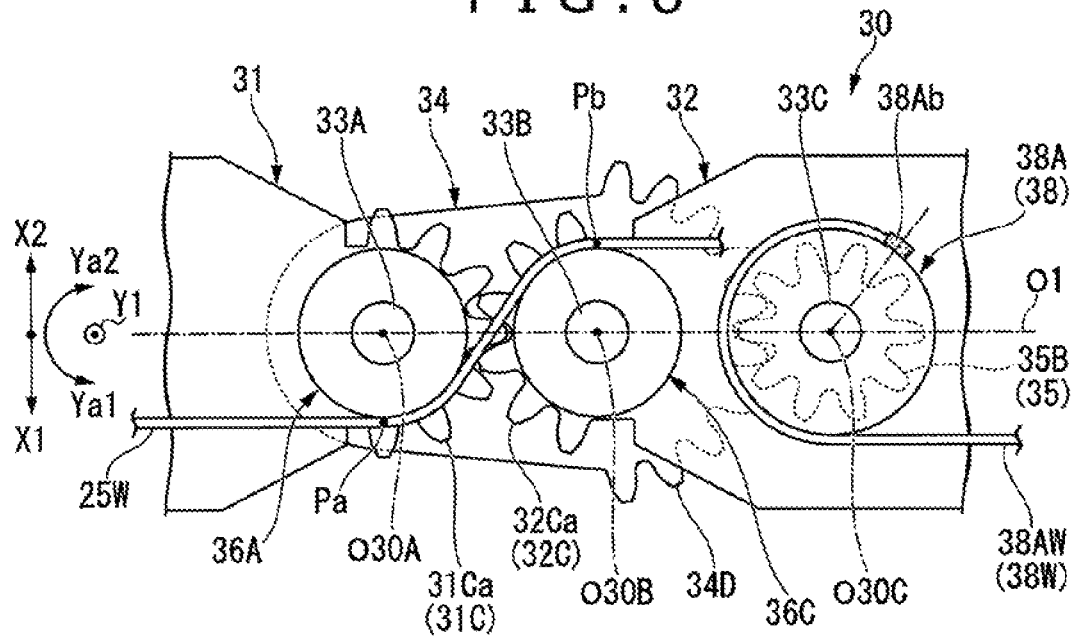
FIG. 8 illustrates the distal-end joint which is in a straight state.
Figure 9:
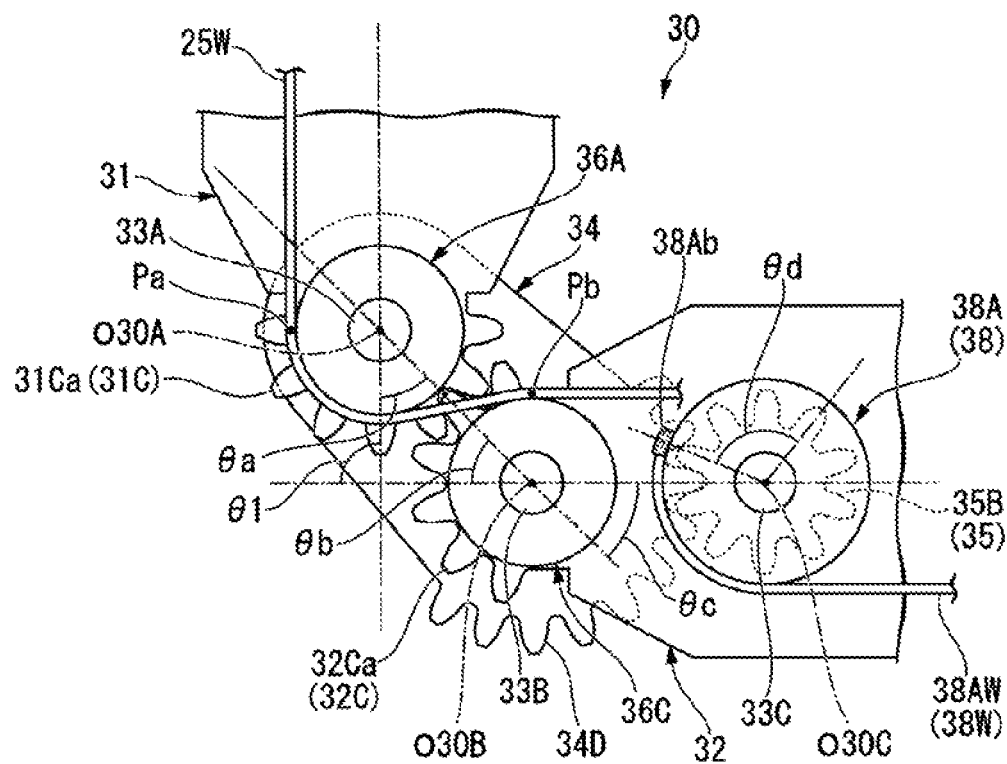
FIG. 9 illustrates the distal-end joint which is in a bent state.

Operation of the distal-end joint 30 which is of the above structure is described with reference to FIGS. 8 and 9. FIG. 8 is a view of the distal-end joint 30 which is in a straight state. FIG. 9 is a view of the distal-end joint 30 which is in a bent state. FIGS. 8 and 9 depict the distal-end joint 30 as viewed from the Y2 direction. In FIGS. 8 and 9, the structure of the distal-end joint 30 is illustrated as simplified. As depicted in FIGS. 8 and 9, a Ya1 direction and a Ya2 direction that is opposite to the Ya1 direction are set as directions of rotation around the Y1 direction.

As depicted in FIG. 8, when the operating wire 38AW is pulled toward the proximal-end side while the distal-end joint 30 is in a straight state, the gear 35B attached to the pulley 38A is turned counterclockwise as viewed from the Y2 direction, i.e., in the Ya1 direction, about the axis O30C. Since the gear 35B is held in mesh with the gear 34D of the intermediate connector 34, the gear 34D is turned in the Ya2 direction about the axis O30B upon angular movement of the gear 35B. In other words, the intermediate connector 34 is turned in the Ya2 direction about the axis O30B with respect to the proximal-end connector 32. At this time, the turn shaft 33A, i.e., the axis O30A, is also turned in unison with the intermediate connector 34 in the Ya2 direction about the axis O30B. Furthermore, since the gear 31C of the distal-end connector 31 is held in mesh with the gear 32C of the proximal-end connector 32, the gear 31C is turned in the Ya2 direction about the axis O30A upon angular movement of the intermediate connector 34. In other words, the distal-end connector 31 is turned in the Ya2 direction about the axis O30A with respect to the intermediate connector 34. The operation described herein brings the distal-end joint 30 into a state in which it is bent in the Ya2 direction, as depicted in FIG. 9. For changing the distal-end joint 30 from the bent state to the straight state or for bending the distal-end joint 30 in the Ya1 direction from the straight state, the operating wire 38BW is pulled toward the proximal-end side. The gear 35B attached to the pulley 38B is now turned in the Ya2 direction about the axis O30C in a manner which is a reversal of the above process. The various components operate in a manner which is a reversal of the above processes thereof, bending the distal-end joint 30 in the Ya1 direction.

The process of bending the distal-end joint 30 is now described in greater detail. It is assumed that the radius of the pitch circle of the gear 31C is represented by Ra, the radius of the pitch circle of the gear 32C by Rb, the radius of the pitch circle of the gear 34D by Rc, and the radius of the pitch circle of the gear 35B by Rd. When the gear 35B is turned an angle θd in the Ya1 direction about the axis O30C, if the gear 34D is turned an angle θc in the Ya2 direction about the axis O30B with respect to the distal-end connector 32, then the angle θc is expressed by the following equation:

$$\theta c = \theta d \times Rd/Rc \quad (1)$$

At this time, if the gear 31C is turned an angle θa in the Ya2 direction about the axis O30A with respect to the intermediate connector 34 and the gear 32C is turned an angle θb in the Ya1 direction about the axis O30B with respect to the intermediate connector 34, then the angle θa is expressed by the following equation:

$$\theta a = \theta b \times Rb/Ra \quad (2)$$

According to the present embodiment, the pitch circle diameter of the gear 31C is the same as the pitch circle diameter of the gear 32C. Furthermore, the magnitude of the angle θb is the same as the magnitude of the angle θc. Therefore, the equation (2) is rewritten as:

$$\theta a = \theta b = \theta c \quad (3)$$

Therefore, the angle θ1 through which the distal-end connector 31 is turned with respect to the proximal-end connector 32 is expressed by the following equation:

$$\theta 1 = \theta a + \theta c \theta 2 \theta c \quad (4)$$

Consequently, the angle θ1 through which the distal-end connector 31 is turned with respect to the proximal-end connector 32 is twice the angle θc through which the intermediate connector 34 is turned with respect to the proximal-end connector 32.

If it is assumed that the torque of the gear 34D at the moment it is turned is represented by Tc and the torque of the gear 35B at the moment it is turned is represented by Td, then the torque Tc is expressed by the following equation:

$$Tc = Td \times Rc/Rd \quad (5)$$

According to the present embodiment, since the pitch circle diameter of the gear 35B is smaller than the pitch circle diameter of the gear 34D, Rc/Rd (speed reduction ratio)>1. With the speed reduction ratio being thus large, the torque Td of the gear 35B is reduced with respect to the torque Tc of the gear 34D. Therefore, the tension that is applied to the operating wire 38AW and the operating wire 38BW for turning the gear 35B is reduced. With respect to a double joint, its bending does not affect the length of a path along which an operating wire extends in the double joint. For example, the length of a path between a point Pa and a point Pb depicted in FIG. 8 for the operating wire 25W wound around the pulley 36A and the pulley 36C is equal to the length of a path between the point Pa and the point Pb at the time the distal-end joint 30 is bent as depicted in FIG. 9. Therefore, the distal-end joint 30 can be bent independently of how the paired grippers 11 are operated.

Inasmuch as the distal-end joint 30 is constructed as described above, it is resistant to disturbances such as external forces applied to skew the shafts of the joint. For example, if the two grippers 11 grip a target object with a large force, then the tension applied to the operating wire 26W is large. The tension tends to apply a force through the pulley 36B and the pulley 36D around which the operating wire 26W is wound to the turn shaft 33A and the turn shaft 33B, tending to skew the turn shaft 33A and the turn shaft 33B in a manner to increase the distance between the turn shaft 33A and the turn shaft 33B. If the turn shaft 33A and the turn shaft 33B are skewed into a mutually unbalanced positional relation, then since the gear 31C and the gear 32C are also skewed while in mesh with each other, the frictional force acting therebetween increases. As a result, the controllability and operability of the end effector 10 is lowered.

According to conventional double joints, a gear of a distal-end connector through which a turn shaft is inserted and a gear of a proximal-end connector through which another turn shaft is inserted are held in mesh with each other and support each other thereby to counteract forces acting on the turn shafts and moments caused by the forces, keeping the turn shafts in a desired posture. In view of the features described herein, in the distal-end joint 30 according the present embodiment, the rotation transmitter 31A of the distal-end connector 31 is divided into the upper rotation transmitter 31Aa having the upper gear 31Ca and the lower rotation transmitter 31Ab having the lower gear 31Cb, and the rotation transmitter 32A of the proximal-end connector 32 is divided into the upper rotation transmitter 32Aa having the upper gear 32Ca and the lower rotation transmitter 32Ab having the lower gear 32Cb. The intermediate connector 34 is disposed between the upper rotation transmitter 31Aa and the lower rotation transmitter 31Ab and also disposed between the upper rotation transmitter 32Aa and the lower rotation transmitter 32Ab. With this arrangement, the dimension of the gear 31C of the rotation transmitter 31A in the Y1 direction and the dimension of the gear 32C of the rotation transmitter 32A in the Y1 direction are substantially increased. Specifically, the upper gear 31Ca and the upper gear 32Ca are disposed in a region displaced in the Y1 direction depending on the dimension in the Y1 direction of the space in which the intermediate connector 34 is disposed, and the lower gear 31Cb and the lower gear 32Cb are disposed in a region displaced in the Y2 direction depending on the dimension of the above space. As a result, the overall dimension of the gear 31C in the Y1 direction and the overall dimension of the gear 32C in the Y1 direction are large. Moreover, the upper gear 31Ca and the upper gear 32Ca are held in mesh with each other at a position closer to the ends of the turn shaft 33A and the turn shaft 33B in the Y1 direction, and the lower gear 31Cb and the lower gear 32Cb are held in mesh with each other at a position closer to the ends of the turn shaft 33A and the turn shaft 33B in the Y2 direction. Therefore, the gear 31C and the gear 32C are able to keep the turn shaft 33A and the turn shaft 33B by the above-stated force in a more reliable posture against moments acting on the turn shaft 33A and the turn shaft 33B. The distal-end joint 30 is thus of a structure resistant to disturbances.

In addition, according to the present embodiment, the intermediate connector 34 is disposed between the upper rotation transmitter 31Aa and the lower rotation transmitter 31Ab and also is disposed between the upper rotation transmitter 32Aa and the lower rotation transmitter 32Ab, and simultaneously supports central portions of the turn shaft 33A and the turn shaft 33B in the Y1 direction. Consequently, when the intermediate connector 34 is turned about the axis O30B by the gear 35B, it reduces a moment acting to skew the turn shaft 33A with respect to the turn shaft 33B under a force that the intermediate connector 34 applies to the turn shaft 33A to move the turn shaft 33A.

Figure 10:
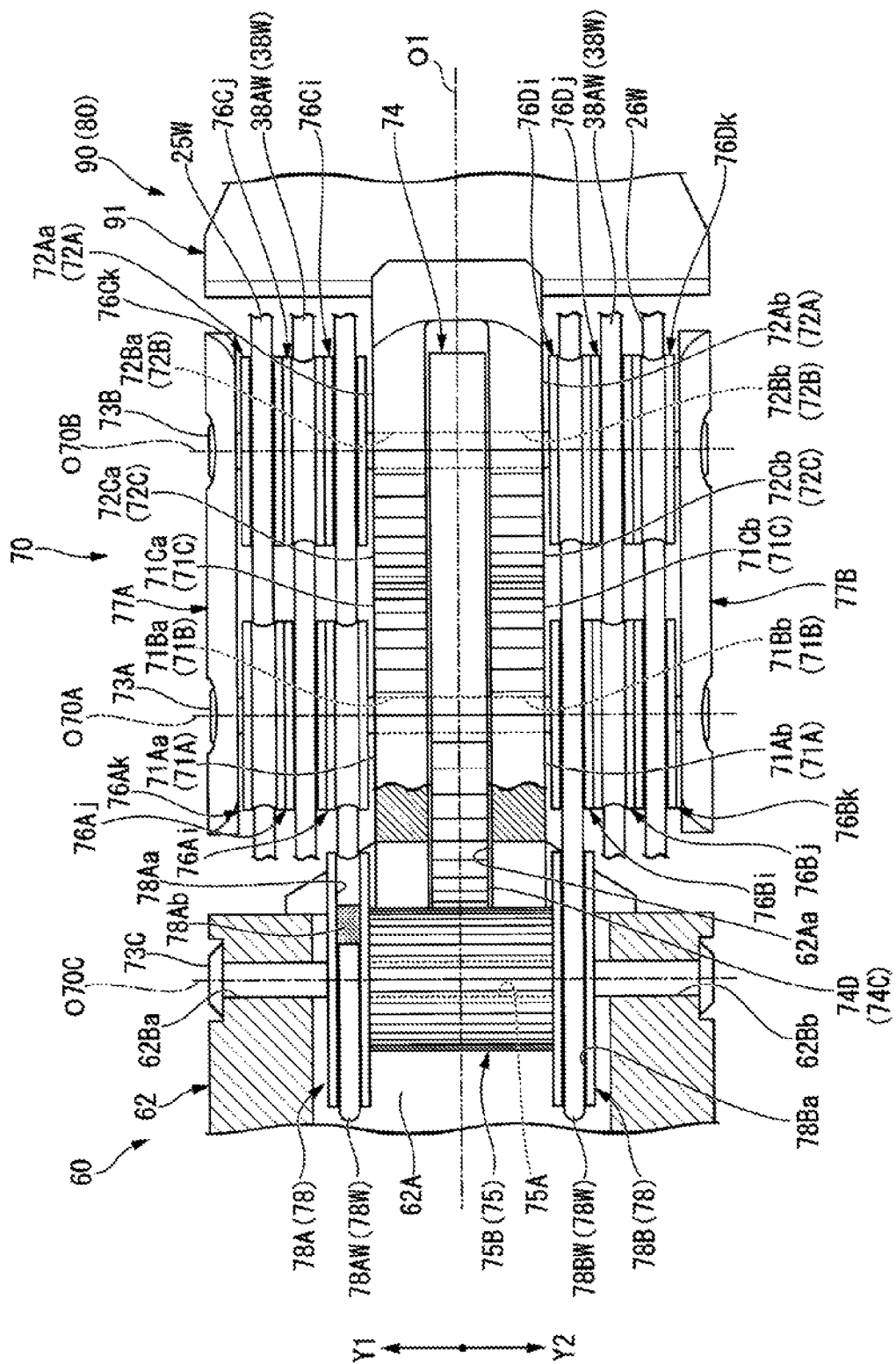
FIG. 10 is a view, partly in cross section, depicting the structure of an intermediate joint of the medical instrument.
Figure 11:
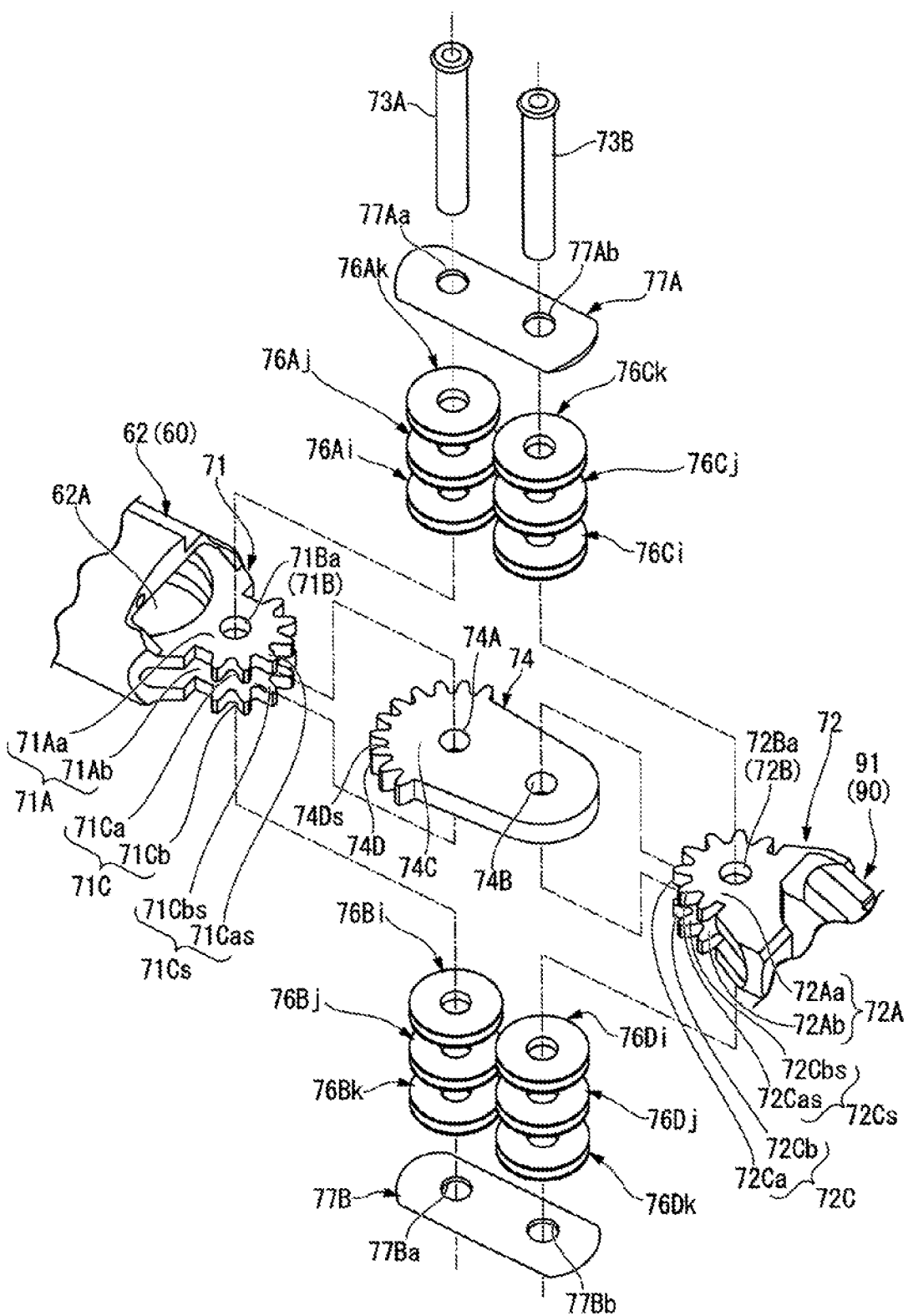
FIG. 11 is an exploded perspective view of the intermediate joint of the medical instrument depicted in FIG. 1.
Figure 12:
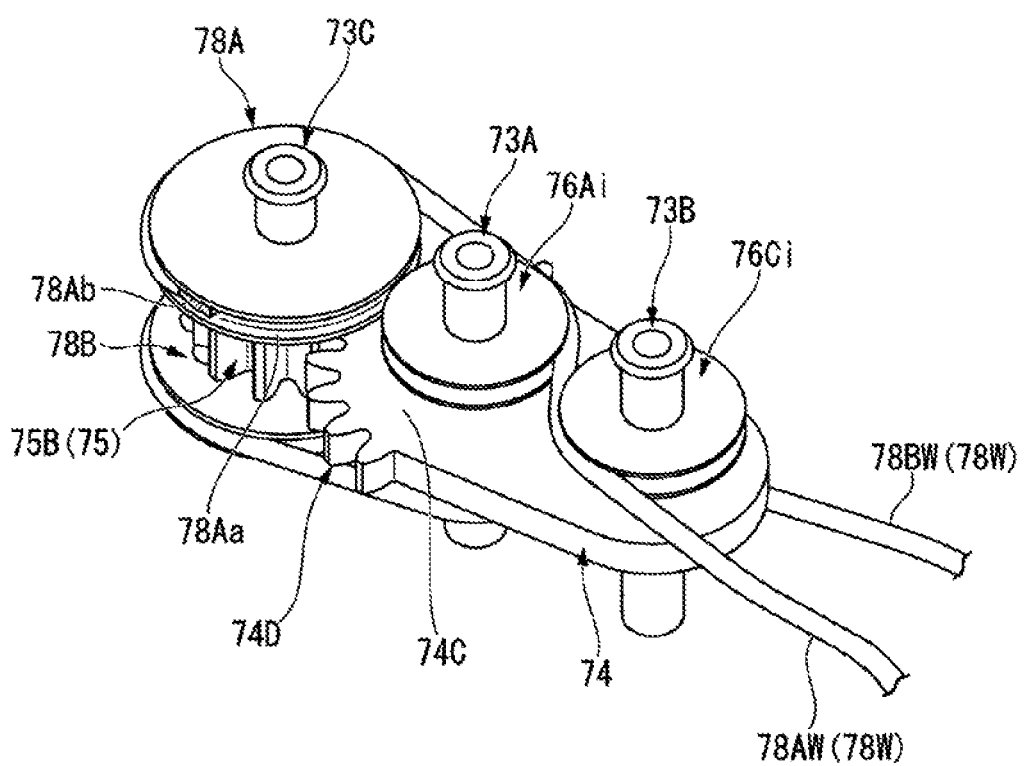
FIG. 12 is a perspective view of the structure of an intermediate connector and a rotation transmitter of the intermediate joint.

The intermediate joint 70 is now described with reference to FIGS. 10 through 14. FIG. 10 is a view, partly in cross section, depicting the structure of the intermediate joint 70. FIG. 11 is an exploded perspective view of the intermediate joint 70. FIG. 12 is a perspective view of the structure of an intermediate connector 74 and a rotation transmitter 75 of the intermediate joint 70. The intermediate joint 70 includes a double joint that is bendable about the Y1 direction. The intermediate joint 70 has an axis O70A, an axis O70B, and an axis O70C. The axis O70B is spaced from the axis O70A and extends parallel to the axis O70A. The axis O70B is disposed more closely to the proximal-end side than the axis O70A. The axis O70C is spaced from the axes O70A and O70B and extends parallel to the axes O70A and O70B. The axis O70C is disposed more closely to the proximal-end side than the axis O70A and is attached in position with respect to the axis O70A. According to the present embodiment, the axis O70A, the axis O70B, and the axis O70C are perpendicular to the longitudinal axis O1 and parallel to the Y1 direction.

The intermediate joint 70 has a distal-end connector 71, a proximal-end connector 72, the intermediate connector 74, and the rotation transmitter 75. Whereas on the distal-end joint 30 the rotation transmitter 35 is disposed more closely to the proximal-end side than the intermediate connector 34, on the intermediate joint 70 the rotation transmitter 75 is disposed more closely to the distal-end side than the intermediate connector 74. The distal-end connector 71 is attached to a proximal-end side of a proximal-end portion 62 of the arm 60. The distal-end connector 71 has a rotation transmitter 71A provided on a proximal-end side thereof. The rotation transmitter 71A is angularly movable about the axis O70A. The rotation transmitter 71A has a circular hole 71B defined therein which extends in the Y1 direction therethrough with the axis O70A at its center. A cylindrical turn shaft 73A with the axis O70A defining as its central axis and extends in the Y1 direction, is inserted through the circular hole 71B. The turn shaft 73A is supported by the rotation transmitter 71A for relative angular movement about the axis O70A through the circular hole 71B. In other words, the rotation transmitter 71A is angularly movable about the axis O70A with respect to the turn shaft 73A.

The rotation transmitter 71A is divided into an upper rotation transmitter 71Aa and a lower rotation transmitter 71Ab in a direction along the axis O70A, i.e., in the Y1 direction or the Y2 direction. The upper rotation transmitter 71Aa and the lower rotation transmitter 71Ab are spaced apart from one another in the Y1 direction and are disposed parallel to each other with the longitudinal axis O1 interposed therebetween. The upper rotation transmitter 71Aa is disposed on one side of the longitudinal axis O1 in the Y1 direction, and the lower rotation transmitter 71Ab is disposed on the other side of the longitudinal axis O1 in the Y2 direction. The upper rotation transmitter 71Aa has a circular hole 71Ba defined therein as part of the circular hole 71B, which extends in the Y1 direction therethrough with the axis O70A at its center, and the lower rotation transmitter 71Ab has a circular hole 71Bb defined therein as part of the circular hole 71B, which extends in the Y1 direction therethrough with the axis O70A at its center. The turn shaft 73A is inserted through the circular hole 71Ba and the circular hole 71Bb. The rotation transmitter 71A has a gear 71C including a sectorial region 71Cs about the axis O70A at its center and teeth formed on the arc of the sectorial region 71Cs. The upper rotation transmitter 71Aa has an upper gear 71Ca as part of the gear 71C, and the lower rotation transmitter 71Ab has a lower gear 71Cb as part of the gear 71C. The upper gear 71Ca has a sectorial region 71Cas as part of the sectorial region 71Cs, and the lower gear 71Cb has a sectorial region 71Cbs as part of the sectorial region 71Cs. The gear 71C is held in mesh with a gear 72C of a rotation transmitter 72A and will be described in greater detail hereinafter. Specifically, the upper gear 71Ca is held in mesh with an upper gear 72Ca of the gear 72C, whereas the lower gear 71Cb is held in mesh with a lower gear 72Cb of the gear 72C. The rotation transmitter 71A and the rotation transmitter 72A are thus operatively connected to one another such that they are angularly movable in combined relation to one another.

The proximal-end connector 72 is provided on a distal-end side of the arm 80 and is attached to the arm 80. According to the present embodiment, the proximal-end connector 72 is attached to a distal-end portion 91 of the proximal-end joint 90 of the arm 80. The proximal-end connector 72 has the rotation transmitter 72A provided on a distal-end side thereof. The rotation transmitter 72A is angularly movable about the axis O70B. Specifically, the rotation transmitter 72A has a circular hole 72B defined therein which extends in the Y1 direction therethrough with the axis O70B at its center. A cylindrical turn shaft 73B with the axis O70B defining as its central axis and extends in the Y1 direction, is inserted through the circular hole 72B. The turn shaft 73B is supported by the rotation transmitter 72A for relative angular movement about the axis O70B through the circular hole 72B. In other words, the rotation transmitter 72A is angularly movable about the axis O70B with respect to the turn shaft 73B. The rotation transmitter 72A is divided into an upper rotation transmitter 72Aa and a lower rotation transmitter 72Ab in a direction along the axis O70B, i.e., in the Y1 direction (or the Y2 direction). The upper rotation transmitter 72Aa and the lower rotation transmitter 72Ab are disposed in a manner similar to the upper rotation transmitter 71Aa and the lower rotation transmitter 71Ab, respectively, of the rotation transmitter 71A. The upper rotation transmitter 72Aa has a circular hole 72Ba defined therein as part of the circular hole 72B, and the lower rotation transmitter 72Ab has a circular hole 72Bb defined therein as part of the circular hole 72B.

The rotation transmitter 72A has a gear 72C including a sectorial region 72Cs about the axis O70B at its center and teeth formed on the arc of the sectorial region 72Cs. The upper rotation transmitter 72Aa has an upper gear 72Ca as part of the gear 72C, and the lower rotation transmitter 72Ab has a lower gear 72Cb as part of the gear 72C. The upper gear 72Ca has a sectorial region 72Cas as part of the sectorial region 72Cs, and the lower gear 72Cb has a sectorial region 72Cbs as part of the sectorial region 72Cs.

According to the present embodiment, the pitch circle diameter of the gear 71C (e.g., the upper gear 71Ca and the lower gear 71Cb) is the same as the pitch circle diameter of the gear 72C (e.g., the upper gear 72Ca and the lower gear 72Cb). The dimension of the gear 71C in the Y1 direction is the same as the dimension of the gear 72C in the Y1 direction. In other words, the dimension of the upper gear 71Ca in the Y1 direction and the dimension of the upper gear 72Ca in the Y1 direction are equal to one another, and the dimension of the lower gear 71Cb in the Y1 direction and the dimension of the lower gear 72Cb in the Y1 direction are equal to one another. The intermediate connector 74 is angularly movable about the axis O70A and is also angularly movable about the axis O70B. According to the present embodiment, the intermediate connector 74 is of the same structure as the intermediate connector 34 of the distal-end joint 30 except that a rotation transmitter 74C is provided on a distal-end side thereof. The turn shaft 73A is inserted through a circular hole 74A defined in the distal-end side of the intermediate connector 74, for relative angular movement about the axis O70A. The turn shaft 73B is inserted through a circular hole 74B defined in a distal-end side of the intermediate connector 74, for relative angular movement about the axis O70B.

According to the present embodiment, the distal-end side of the intermediate connector 74 is disposed between the upper rotation transmitter 71Aa and the lower rotation transmitter 71Ab of the rotation transmitter 71A. The proximal-end side of the intermediate connector 74 is disposed between the upper rotation transmitter 72Aa and the lower rotation transmitter 72Ab of the rotation transmitter 72A. The intermediate connector 74 has the rotation transmitter 74C provided on a distal-end portion thereof. The rotation transmitter 74C is operatively connected to the rotation transmitter 75 such that the rotation transmitter 74C is angularly moved about the axis O70A in combined relation to the rotation transmitter 75. According to the present embodiment, the rotation transmitter 74C has a gear 74D including a sectorial region 74Ds about the axis O70B at its center and teeth formed on the arc of the sectorial region 74Ds. The gear 74D is held in mesh with a gear 75B of the rotation transmitter 75 to be described later. Therefore, angular movement of the rotation transmitter 75 is transmitted through the gear 75B and the gear 74D to the rotation transmitter 74C. The rotation transmitter 74C is thus angularly movable about the axis O70A in combined relation to the rotation transmitter 75.

A pulley 76Ai, a pulley 76Aj, and a pulley 76Ak are successively arranged along the Y1 direction on the side of the upper rotation transmitter 71Aa of the rotation transmitter 71A in the Y1 direction. A pulley 76Bi, a pulley 76Bj, and a pulley 76Bk are successively arranged along the Y2 direction on the side of the lower rotation transmitter 71Ab of the rotation transmitter 71A in the Y2 direction. A pulley 76Ci, a pulley 76Cj, and a pulley 76Ck are successively arranged along the Y1 direction on the side of the upper rotation transmitter 72Aa of the rotation transmitter 72A in the Y1 direction. A pulley 76Di, a pulley 76Dj, and a pulley 76Dk are successively arranged in the order named along the Y2 direction on the side of the lower rotation transmitter 72Ab of the rotation transmitter 72A in the Y2 direction. The pulley 76Ai, the pulley 76Aj, the pulley 76Ak, the pulley 76Bi, the pulley 76Bj, the pulley 76Bk, the pulley 76Ci, the pulley 76Cj, the pulley 76Ck, the pulley 76Di, the pulley 76Dj, and the pulley 76Dk may each be a pulley which is of the same structure as the pulley 36A, the pulley 36B, the pulley 36C, and/or the pulley 36D of the distal-end joint 30.

The turn shaft 73A is inserted through a circular hole in the pulley 76Ai, a circular hole in the pulley 76Aj, a circular hole in the pulley 76Ak, a circular hole in the pulley 76Bi, a circular hole in the pulley 76Bj, and a circular hole in the pulley 76Bk for relative angular movement about the axis O70A. The turn shaft 73B is inserted through a circular hole in the pulley 76Ci, a circular hole in the pulley 76Cj, a circular hole in the pulley 76Ck, a circular hole in the pulley 76Di, a circular hole in the pulley 76Dj, and a circular hole in the pulley 76Dk for relative angular movement about the axis O70B.

An operating wire 78AW extending from a pulley 78A is wound in a pulley groove of the pulley 76Ai and a pulley groove of the pulley 76Ci. The operating wire 38AW extending from the pulley 38A of the distal-end joint 30 is wound in a pulley groove of the pulley 76Aj and a pulley groove of the pulley 76Cj. The operating wire 25W extending from the pulley 36A of the distal-end joint 30 is wound in a pulley groove of the pulley 76Ak and a pulley groove of the pulley 76Ck.

An operating wire 78BW extending from a pulley 78B is wound in a pulley groove of the pulley 76Bi and a pulley groove of the pulley 76Di. The operating wire 38BW extending from the pulley 38B of the distal-end joint 30 is wound in a pulley groove of the pulley 76Bj and a pulley groove of the pulley 76Dj. The operating wire 26W extending from the pulley 36B of the distal-end joint 30 is wound in a pulley groove of the pulley 76Bk and a pulley groove of the pulley 76Dk. According to the present embodiment, as depicted in FIG. 10, the pulley 76Ai and the pulley 76Ci, the pulley 76Aj and the pulley 76Cj, the pulley 76Ak and the pulley 76Ck, the pulley 76Bi and the pulley 76Di, the pulley 76Bj and the pulley 76Dj, and the pulley 76Bk and the pulley 76Dk are disposed in the same positions as each other in the Y1 direction. In addition, the pulley 76Aj and the pulley 76Cj are disposed in the same position as the pulley 38A in the Y1 direction. The pulley 76Ak and the pulley 76Ck are disposed in the same position as the pulley 36A and the pulley 36C in the Y1 direction. The pulley 76Bj and the pulley 76Dj are disposed in the same position as the pulley 38B in the Y1 direction. The pulley 76Bk and the pulley 76Dk are disposed in the same position as the pulley 36B and the pulley 36D in the Y1 direction. With this arrangement, the operating wires 25W, 26W, 38AW, and 38BW extend from the distal-end joint 30 through the intermediate joint 70 can smoothly be actuated.

The operating wire 78AW is wound around the pulley 76Ai from the X2 direction and around the pulley 76Ci in the X1 direction such that the operating wire 78AW crosses the longitudinal direction O1 between the pulley 76Ai and the pulley 76Ci as viewed from the Y2 direction. The operating wire 38AW is wound around the pulley 76Aj from the X1 direction and around the pulley 76Cj in the X2 direction such that the operating wire 38AW crosses the longitudinal direction O1 between the pulley 76Aj and the pulley 76Cj as viewed from the Y2 direction. The operating wire 25W is wound around the pulley 76Ak and the pulley 76Ck in the same manner as the operating wire 78AW wound around the pulley 76Ai and the pulley 76Ci. The operating wire 78BW is wound around the pulley 76Bi and the pulley 76Di in the same manner as the operating wire 38AW wound around the pulley 76Aj and the pulley 76Cj. The operating wire 38BW is wound around the pulley 76Bj and the pulley 76Dj in the same manner as the operating wire 78AW wound around the pulley 76Ai and the pulley 76Ci. The operating wire 26W is wound around the pulley 76Bk and the pulley 76Dk in the same manner as the operating wire 38AW wound around the pulley 76Aj and the pulley 76Cj. A support member 77A is provided on the sides of the pulley 76Ak and the pulley 76Ck which face in the Y1 direction. The support member 77A may be of the same structure as the support member 37A of the distal-end joint 30. A support member 77B is provided on the sides of the pulley 76Bk and the pulley 76Dk which face in the Y2 direction. The support member 77B may be of the same structure as the support member 37B of the distal-end joint 30. The turn shaft 73A is inserted through a circular hole 77Aa in the support member 77A and a circular hole 77Ba in the support member 77B for relative angular movement about the axis O70A. The turn shaft 73B is inserted through a circular hole 77Ab in the support member 77A and a circular hole 77Bb in the support member 77B for relative angular movement about the axis O70B. The turn shaft 73A has both ends supported by the support member 77A and the support member 77B through the circular hole 77Aa and the circular hole 77Ba. Likewise, the turn shaft 73B has both ends supported by the support member 77A and the support member 77B through the circular hole 77Ab and the circular hole 77Bb.

With the above structure, the turn shaft 73A interconnects the support member 77A, the pulley 76Ai, the pulley 76Aj, the pulley 76Ak, the rotation transmitter 71A (e.g., the upper rotation transmitter 71Aa and the lower rotation transmitter 71Ab), the intermediate connector 74, the pulley 76Bi, the pulley 76Bj, the pulley 76Bk, and the support member 77B for relative angular movement about the axis O70A. Similarly, the turn shaft 73B interconnects the support member 77A, the pulley 76Ci, the pulley 76Cj, the pulley 76Ck, the rotation transmitter 72A (the upper rotation transmitter 72Aa and the lower rotation transmitter 72Ab), the intermediate connector 74, the pulley 76Di, the pulley 76Dj, the pulley 76Dk, and the support member 77B for relative angular movement about the axis O70B. The distance between the axis O70A and the axis O70B is kept constant by the support member 77A, the intermediate connector 74, and the support member 77B. The rotation transmitter 75 is angularly movable about the axis O70C. Specifically, the rotation transmitter 75 has a circular hole 75A defined therein which extends in the Y1 direction therethrough with the axis O70C at its center. A cylindrical turn shaft 73C with the axis O70C defining as its central axis and extends in the Y1 direction, is inserted through the circular hole 75A. The turn shaft 73C is supported by the rotation transmitter 75 for relative angular movement about the axis O70C through the circular hole 75A. In other words, the rotation transmitter 75 is angularly movable about the axis O70C with respect to the turn shaft 73C. The rotation transmitter 75 is of a cylindrical shape with the axis O70C at its center and has a gear 75B having teeth formed on an outer circumferential surface thereof around the axis O70C. As described hereinbefore, the gear 75B is held in mesh with the gear 74D. The pitch circle diameter of the gear 75B is smaller than the pitch circle diameter of the gear 74D. Therefore, the rotating speed of the gear 74D is smaller than the rotating speed of the gear 75B, and the torque of the gear 74D is larger than the torque of the gear 75B. The intermediate joint 70 has a pulley 78 angularly movable about the axis O70C and an operating wire 78W wound around the pulley 78. The pulley 78 is connected to the gear 75B for angular movement in unison therewith. According to the present embodiment, the pulley 78 includes a pulley 78A and a pulley 78B, and the operating wire 78W includes an operating wire 78AW and an operating wire 78BW.

The pulley 78A and the pulley 78B may each be a pulley which is of the same structure as the pulley 38A or the pulley 38B of the distal-end joint 30. The turn shaft 73C is inserted through a circular hole (not depicted) in the pulley 78A and a circular hole (not depicted) in the pulley 78B for relative angular movement about the axis O70C. The pulley 78A is disposed adjacent to the gear 75B in the Y1 direction and is attached to the gear 75B for angular movement in unison with the gear 75B. The pulley 78A is disposed in the same position as the pulley 76Ai and the pulley 76Ci in the Y1 direction. The pulley 78B is disposed adjacent to the gear 75B in the Y2 direction and is attached to the gear 75B for angular movement in unison with the gear 75B. The pulley 78B is disposed in the same position as the pulley 76Bi and the pulley 76Di in the Y1 direction. An operating wire 78AW is wound in a pulley groove 78Aa of the pulley 78A. The operating wire 78AW has one end fastened to the pulley groove 78Aa by a fastener 78Ab. The other end of the operating wire 78AW is connected to the power transmitter of the medical instrument 1. The operating wire 78AW is wound in the pulley groove 78Aa counterclockwise as viewed from the Y2 direction from the other end toward one end of the operating wire 78AW. An operating wire 78BW is wound in a pulley groove 78Ba of the pulley 78B. The operating wire 78BW has one end fastened to the pulley groove 78Ba by a fastener (not depicted). The other end of the operating wire 78BW is connected to the power transmitter of the medical instrument 1. The operating wire 78BW is wound in the pulley groove 78Ba clockwise as viewed from the Y2 direction from the other end toward one end of the operating wire 78BW. With the above structure, when the operating wire 78AW is pulled toward the proximal-end side, the pulley 78A and the gear 75B are turned clockwise as viewed from the Y2 direction. When the operating wire 78BW is pulled toward the proximal-end side, the pulley 78B and the gear 75B are turned counterclockwise as viewed from the Y2 direction.

According to the present embodiment, the outside diameter of the pulley 78A and the pulley 78B is larger than the pitch circle diameter of the gear 75B. Consequently, the tension of the operating wire 78AW and the operating wire 78BW which is required to turn the gear 75B is reduced. In addition, a speed reduction occurs between the pulley 78 and the gear 75B. The arm 60 has a housing space 62A defined in the distal-end portion 62 thereof and extending along the longitudinal axis O1. The housing space 62A is disposed in a distal-end side of the distal-end connector 71 attached to the proximal-end portion 62. The housing space 62A is held in communication with a space defined between the upper rotation transmitter 71Aa and the lower rotation transmitter 71Ab of the rotation transmitter 71A, in a direction along the longitudinal axis O1 through an opening 62Aa. The proximal-end portion 62 has a circular hole 62Ba and a circular hole 62Bb defined therein which extend therethrough with the axis O70C at their centers. The circular hole 62Ba and the circular hole 62Bb are held in communication with the housing space 62A and disposed with the housing space 62A interposed therebetween. The rotation transmitter 75, the pulley 78A, and the pulley 78B are disposed in the housing space 62A. The gear 74D of the rotation transmitter 74C is disposed in the housing space 62A through the opening 62Aa and held in mesh with the gear 75B of the rotation transmitter 75. The turn shaft 73C has both ends supported in the circular hole 62Ba and the circular hole 62Bb for relative angular movement about the O70C. The turn shaft 73C is supported on the proximal-end portion 62 through the circular hole 62Ba and the circular hole 62Bb, and the turn shaft 73A is supported on the rotation transmitter 71A of the distal-end connector 71 attached to the proximal-end portion 62. Therefore, the axis O70C is attached in position with respect to the axis O70A.

Figure 13:
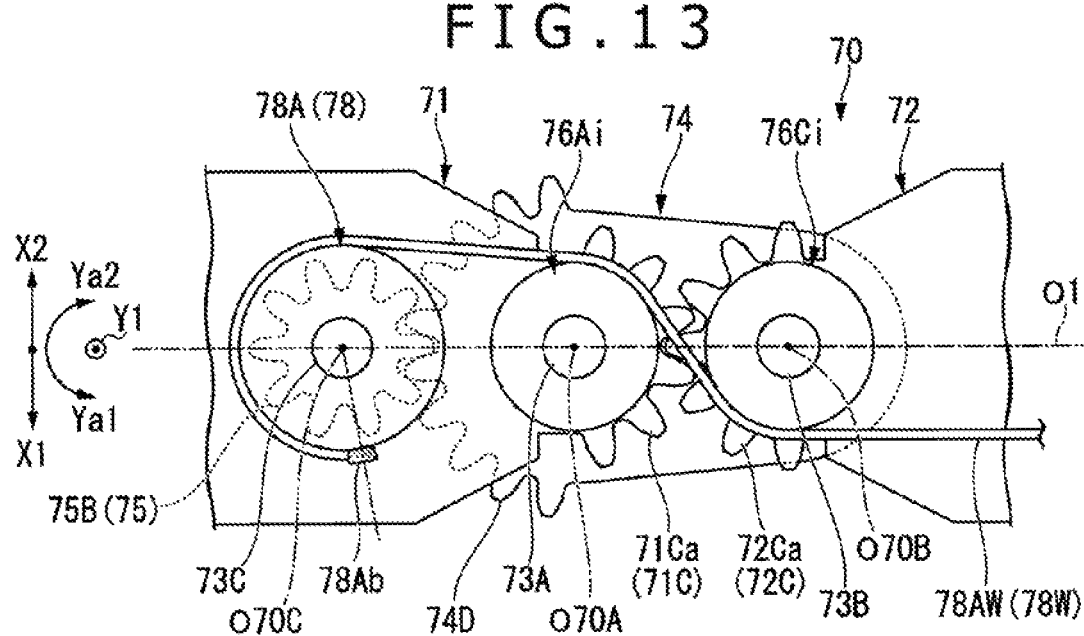
FIG. 13 illustrates the intermediate joint which is in a straight state.
Figure 14:
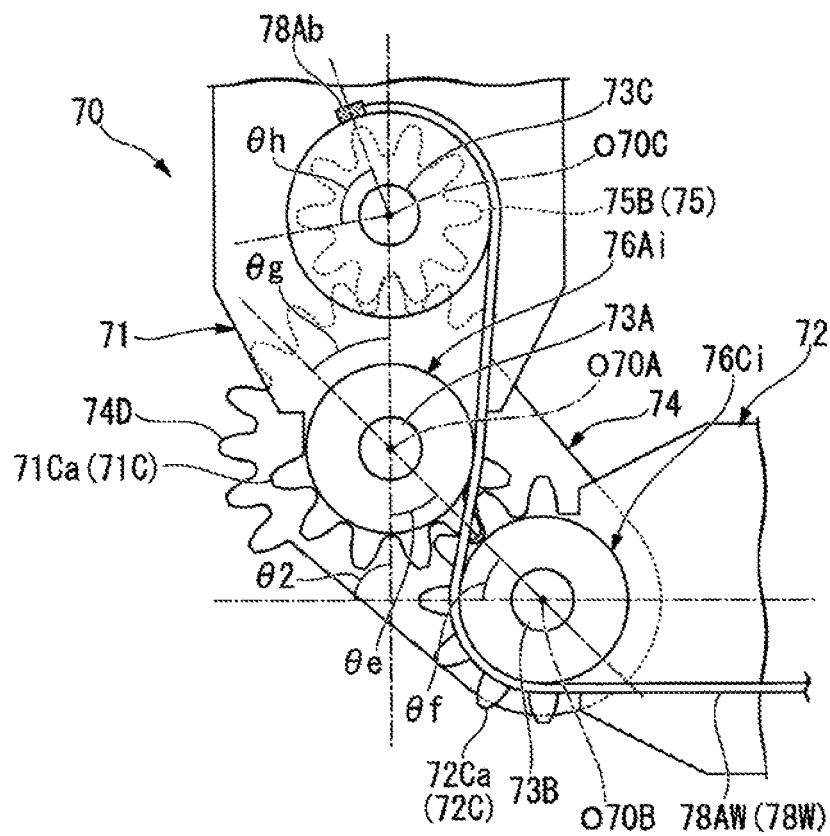
FIG. 14 illustrates the intermediate joint which is in a bent state.

Operation of the intermediate joint 70 which is of the above structure is now described with reference to FIGS. 13 and 14. FIG. 13 is a view of the intermediate joint 70 which is in a straight state. FIG. 14 is a view of the intermediate joint 70 which is in a bent state. FIGS. 13 and 14 depict the intermediate joint 70 as viewed from the Y2 direction. In FIGS. 13 and 14, the structure of the intermediate joint 70 is illustrated as simplified.

As depicted in FIG. 13, when the operating wire 78AW is pulled toward the proximal-end side while the intermediate joint 70 is in a straight state, the gear 75B that attached to the pulley 78A is turned clockwise as viewed from the Y2 direction, i.e., in the Ya2 direction, about the axis O70C. Since the gear 75B is held in mesh with the gear 74D of the intermediate connector 74, the gear 74D is turned in the Ya1 direction about the axis O70A upon angular movement of the gear 75B. In other words, the intermediate connector 74 is turned in the Ya1 direction about the axis O70A with respect to the distal-end connector 71. At this time, the turn shaft 73B, i.e., the axis O70B, is also turned in unison with the intermediate connector 74 in the Ya1 direction about the axis O70A. Furthermore, since the gear 72C of the proximal-end connector 72 is held in mesh with the gear 71C of the distal-end connector 71, the gear 72C is turned in the Ya1 direction about the axis O70B upon angular movement of the intermediate connector 74. In other words, the proximal-end connector 72 is turned in the Ya1 direction about the axis O70B with respect to the intermediate connector 74. The operation described herein brings the intermediate joint 70 into a state in which it is bent in the Ya1 direction with respect to the distal-end connector 71, as depicted in FIG. 14, or stated otherwise, into a state in which it is bent in the Ya2 direction with respect to the proximal-end connector 72. For changing the intermediate joint 70 from the bent state to the straight state or for bending the intermediate joint 70 in the Ya1 direction from the straight state, the operating wire 78BW is pulled toward the proximal-end side. The gear 75B that attached to the pulley 78B is now turned in the Ya1 direction about the axis O70C in a manner which is a reversal of the above process. The various components operate in a manner which is a reversal of the above processes thereof, bending the intermediate joint 70 in the Ya1 direction.

The above process of bending the intermediate joint 70 is now described in greater detail. It is assumed that the radius of the pitch circle of the gear 71C is represented by Re, the radius of the pitch circle of the gear 72C by Rf, the radius of the pitch circle of the gear 74D by Rg, and the radius of the pitch circle of the gear 75B by Rh. When the gear 75B is turned an angle $\theta h$ in the Ya2 direction about the axis O70C, if the gear 74D is turned an angle $\theta g$ in the Ya1 direction about the axis O70A with respect to the distal-end connector 71, then the angle $\theta g$ is expressed by the following equation:

$$\theta g = \theta h \times Rh/Rg \quad (6)$$

At this time, if the gear 71C is turned an angle $\theta e$ in the Ya2 direction about the axis O70A with respect to the intermediate connector 74 and the gear 72C is turned an angle $\theta f$ in the Ya1 direction about the axis O70B with respect to the intermediate connector 74, then the angle $\theta f$ is expressed by the following equation:

$$\theta f = \theta e \times Re/Rf \quad (7)$$

According to the present embodiment, the pitch circle diameter of the gear 71C is the same as the pitch circle diameter of the gear 72C. Furthermore, the magnitude of the angle $\theta e$ is the same as the magnitude of the angle $\theta g$. Therefore, the equation (7) is rewritten as:

$$\theta f = \theta e = \theta g \quad (8)$$

Therefore, the angle through which the proximal-end connector 72 is turned with respect to the distal-end connector 71, or stated otherwise the angle $\theta 2$ through which the distal-end connector 71 is turned with respect to the proximal-end connector 72, is expressed by the following equation:

$$\theta 2 = \theta g + \theta f = 2\theta g \quad (9)$$

Consequently, the angle $\theta 2$ through which the distal-end connector 71 is turned with respect to the proximal-end connector 72 is twice the angle $\theta g$ through which the intermediate connector 74 is turned with respect to the distal-end connector 71.

If it is assumed that the torque of the gear 74D at the moment it is turned is represented by Tg and the torque of the gear 75B at the moment it is turned is represented by Th, then the torque Tg is expressed by the following equation:

$$Tg = Th \times Rg/Rh \quad (10)$$

According to the present embodiment, since the pitch circle diameter of the gear 75B is smaller than the pitch circle diameter of the gear 74D, Rg/Rh (speed reduction ratio)≥1. With the speed reduction ratio being thus large, the torque Th of the gear 75B is reduced with respect to the torque Tg of the gear 74D. Therefore, the tension that is applied to the operating wire 78AW and the operating wire 78BW for turning the gear 75B is reduced.

As with the distal-end joint 30, the bending of the intermediate joint 70 does not affect the length of a path along which an operating wire extends in the intermediate joint 70.

In the intermediate joint 70, the rotation transmitter 71A (e.g., the upper rotation transmitter 71Aa and the lower rotation transmitter 71Ab) of the distal-end connector 71, the rotation transmitter 72A (e.g., the upper rotation transmitter 72Aa and the lower rotation transmitter 72Ab) of the proximal-end connector 72, and the intermediate connector 74 are disposed in the same manner as with the structure of the distal-end joint 30. As with the case with the distal-end joint 30, therefore, the intermediate joint 70 is resistant to disturbances such as external forces applied to skew the shafts of the joint.

The proximal-end joint 90 is a double joint that is bendable about the Y1 direction. The proximal-end joint 90 has a joint structure that is the same as a joint structure provided by the distal-end joint 30 turned 90 degrees about the longitudinal axis O1, and hence will not be described to avoid redundancy. Though the distal-end joint 30 has two pulleys on each turn shaft, the proximal-end joint 90 has six pulleys on each turn shaft for guiding the operating wires 25W, 26W, 38AW, 38BW, 78AW, and 78BW. The proximal-end joint 90 has a proximal-end side connected to the main body 50.

The main body 50 includes a soft elongate member 51 (see FIG. 2) shaped as a hollow cylinder extending along the longitudinal axis O1 and a power transmitter (not depicted) provided on a proximal end of the elongate member 51. The operating wires 25W, 26W, 38AW, 38BW, 78AW, and 78BW and operating wires for actuating the proximal-end joint 90 are inserted through the elongate member 51 and are connected to the power transmitter. The power transmitter includes a drive source for generating drive power to actuate the operating wires. The power transmitter appropriately actuates the operating wires to bend the distal-end joint 30, the intermediate joint 70, and the proximal-end joint 90. The power transmitter may be an electric motor or the like.

Since the distal-end joint 30, the intermediate joint 70, and the proximal-end joint 90 have the structures described hereinbefore, the medical instrument 1 is able to reduce disturbances imposed on the joints and provide double joints that are resistant to disturbances.

In the distal-end joint 30, the axis O30C is disposed more closely to the proximal-end side than the axis O30B. Therefore, another joint may be provided adjacent to the distal-end side of the distal-end joint 30. In the intermediate joint 70, the axis O70C is disposed more closely to the distal-end side than the axis O70A. Therefore, another joint, e.g., the proximal-end joint 90, may be provided adjacent to the proximal-end side of the intermediate joint 70. In the medical instrument 1 according to the present embodiment, the distances between the joints may be shorter as described hereinbefore. A joint which has the structure of the intermediate joint 70 may be disposed in the position of the distal-end joint 30, and a joint which has the structure of the distal-end joint 30 may be disposed in the position of the intermediate joint 70.

In the distal-end joint 30, since the pitch circle diameter of the gear 35B is smaller than the pitch circle diameter of the gear 34D, the tension that is applied to the operating wire 38AW and the operating wire 38BW for turning the gear 34D is reduced. In addition, since the outside diameter of the pulley 38A and the pulley 38B is larger than the pitch circle diameter of the gear 35B, the tension that is applied to the operating wire 38AW and the operating wire 38BW for turning the gear 34D is further reduced. Consequently, forces applied to the turn shaft 73A and the turn shaft 73B of a joint on the proximal-end side of the distal-end joint 30, e.g., the intermediate joint 70, through the pulleys 76Aj, 76Bj, 76Cj, and 76Dj are reduced.

The main structural details of the medical instrument 1 have been described hereinbefore. In reviewing efforts to increase the precision of operation of the joints of the medical instrument 1, the inventor has found a possibility that when a strong external force is applied to the proximal-end joint 90 to bend the same, the wires for actuating the proximal-end joint 90 are dislodged, making it impossible for the power transmitter to actuate the proximal-end joint 90. This possibility will hereinafter be described in greater detail.

Figure 15:
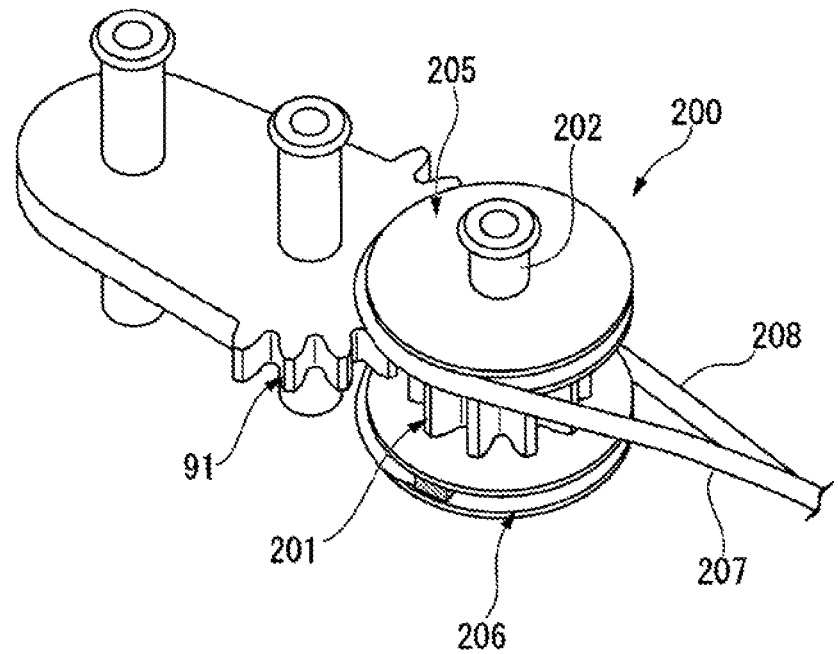
FIG. 15 is a perspective view of the structure of a rotation transmitter in a proximal-end joint of the medical instrument.

FIG. 15 is a view depicting the structure of a rotation transmitter 200 for actuating the proximal-end joint 90. The rotation transmitter 200 has a structure that is generally the same as the rotation transmitter 35. The rotation transmitter 200 includes a gear 201, and a first pulley 205 and a second pulley 206 that are disposed with the gear 201 interposed therebetween in an axial direction thereof.

The gear 201 is held in mesh with a gear 91 that corresponds to the gear 34D in the proximal-end joint 90. Wires (transmitting members) 207 and 208 which are of a slender shape are wound respectively around the pulleys 205 and 206 and have ends attached in position in the same manner as the wires 38AW and 38BW. Portions of the wires 207 and 208 which lead to their ends (one ends) that are not attached to the pulleys 205 and 206 extend tangentially to the pulleys 205 and 206 and away from the pulleys 205 and 206.

Figure 16:
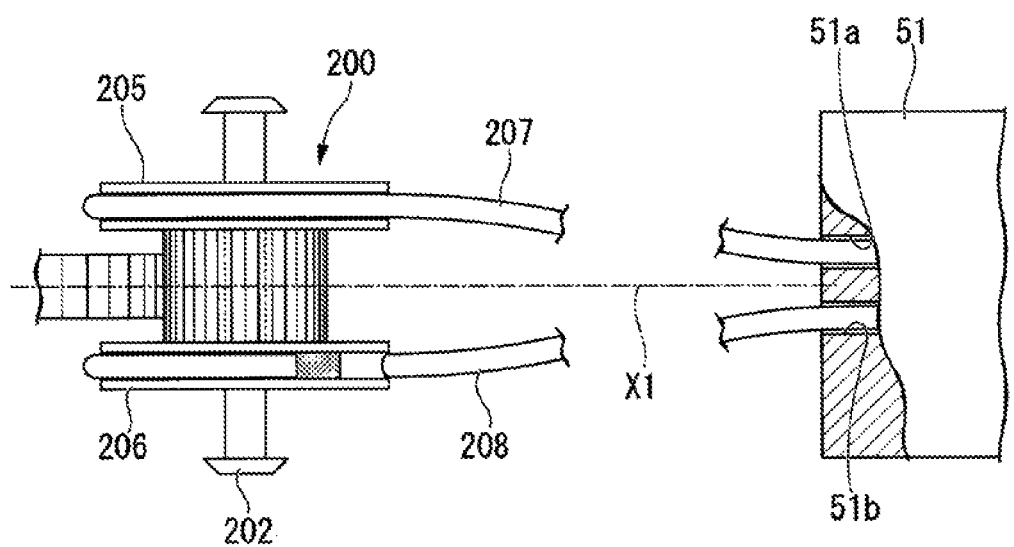
FIG. 16 illustrates the positional relation between pulleys and wires in the rotation transmitter depicted in FIG. 15.

FIG. 16 schematically depicts the positional relation between the rotation transmitter 200 and the wires 207 and 208. The wires 207 and 208 are inserted through lumens 51a and 51b defined in the elongate member 51. Since the lumens 51a and 51b are defined in positions near an axis X1 of the elongate member 51, the wires 207 and 208 extending from the pulleys 205 and 206 are progressively displaced toward one side along the directions in which a rotational shaft 202 of the pulleys 205 and 206 extends and are progressively closer to the axis X1 as the wires 207 and 208 go away from the pulleys 205 and 206.

While the medical instrument 1 is being actuated by the power transmitter, the wires 207 and 208 are hardly slackened and are almost not dislodged off the pulleys around which they are wound. On the other hand, when the user manually bends the proximal-end joint 90 directly by applying an external force thereto, the wire that extends outside of the bend is not slackened because a force tending to extend the wire acts thereon due to rotation of the pulley, whereas the wire that extends inside of the bend is slackened due to rotation of the pulley because the wire is not pulled by the power transmitter. The slackened portions of the wires 207 and 208 have room to move in the rotation transmitter 200. In case the pitch circle diameter of the gear 201 is smaller than the diameter of the pulleys 205 and 206 for achieving a speed reduction, there exists a space between the pulley 205 and the pulley 206 and around the gear 201 for the wires to move therein. The space is relatively small in an area next to the gear 201 which is closer to the distal-end side of the medical instrument 1 because the gear 201 meshes with the gear 91 in that area. However, an area next to the gear 201 which is closer to the proximal-end side of the medical instrument 1 includes the wires 207 and 208 extending therein, but does not have other members for preventing the wires 207 and 208 from moving therein, so that the slackened portions of the wires 207 and 208 tend to be displaced in that area. In addition, inasmuch as the proximal-end portions of the wires 207 and 208 are displaced toward the axis X1, they are liable to be displaced in directions to become closer to the gear 201. When the slackened portions of the wires are largely displaced, the wires are eventually dislodged off the pulleys. When the wires are dislodged off the pulleys, since the pulleys are not turned even if the power transmitter actuates the wires, the distal-end joint 90 fails to operate.

One way to reduce the above possibility would be to increase the pitch circle diameter of the gear 201 to reduce the space around the gear. However, this approach makes it difficult to cause a speed reduction between the pulleys and the gear, and hence is not preferred for increasing the precision of operation of the medical instrument 1.

According to the prior art that prevents a wire wound around a pulley from being dislodged, it has been known to deepen a pulley groove defined in the pulley or to provide walls on both sides of a pulley groove in widthwise directions thereof.

However, the deepened pulley groove results in a reduction in the substantial diameter of the pulley, making it difficult to cause a speed reduction between the pulley and the gear, and hence the deepened pulley is not preferred for increasing the precision of operation of the medical instrument 1.

The walls are not preferred from the standpoint of making the medical instrument 1 smaller in diameter because the walls tend to increase the outside diameter of the pulley. Furthermore, the walls are effective to prevent the wire from moving only in the vicinity of the pulley, and have difficulty in sufficiently restraining the proximal-end side of the wire which extends tangentially to the pulley and away from the pulley from moving along a direction in which the rotational shaft 202 extends. Movement of the proximal-end side of the wire away from the pulley serves as a trigger for dislodging the slackened wire off the pulley.

In view of the premise of both attempts at making the medical instrument 1 smaller in diameter and increasing the precision of operation thereof, therefore, any of the proposed measures are not enough. The inventor of the present disclosure has been successful in making the medical instrument 1 smaller in diameter and increasing the precision of operation thereof by preventing the wire from being dislodged off the pulley groove according to an approach that is totally different from the proposals described above.

Figure 17:
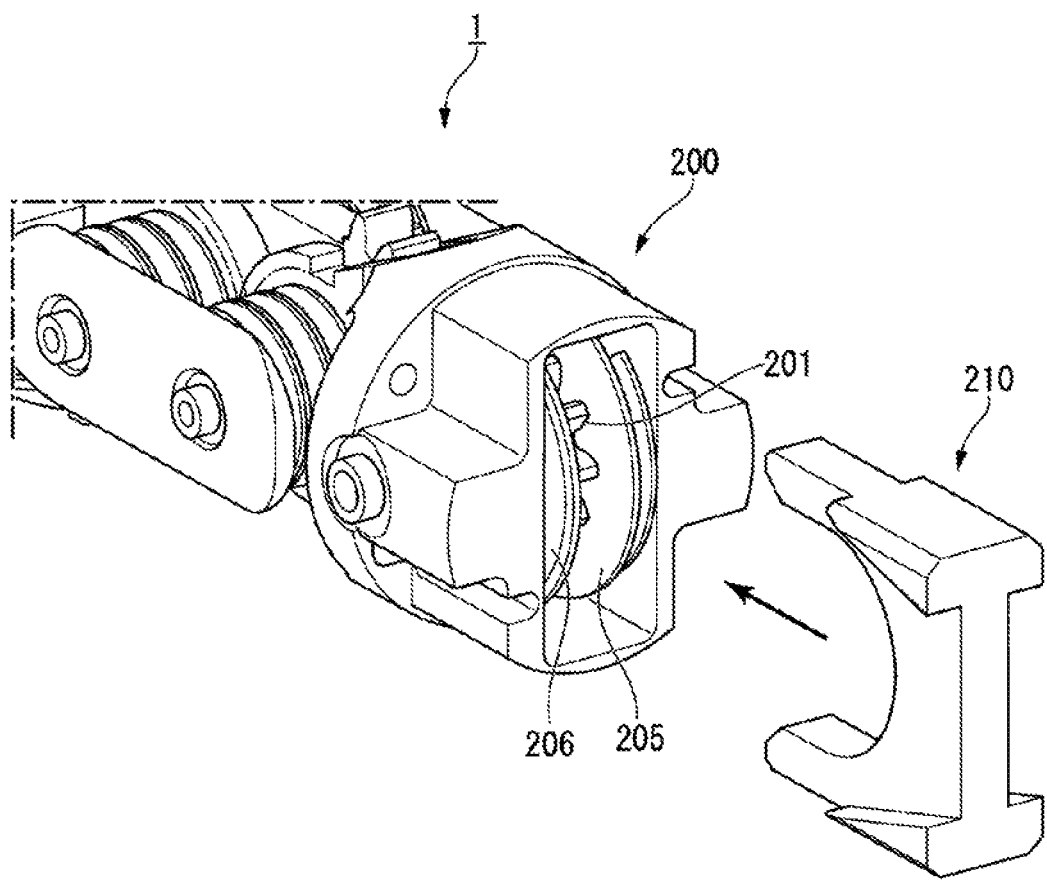
FIG. 17 illustrates the rotation transmitter depicted in FIG. 15 and a spacer.

As depicted in FIG. 17, the medical instrument 1 according to the present embodiment includes a spacer (dislodgement guard) 210 disposed between the pulleys 205 and 206 of the rotation transmitter 200 at a position that is offset from the pulleys 205 and 206 along the direction in which the rotational shaft 202 extends as depicted in FIGS. 15 and 16. The spacer 210 is effective to prevent the wires 207 and 208 from being dislodged off the pulleys 205 and 206 without changing the shapes and dimensions of the pulleys 205 and 206 and the gear 201. The spacer 210 is disposed in the position offset along the direction in which the rotational shaft 202 extends, also with respect to the portions of the wires 207 and 208 that extend tangentially to the pulleys 205 and 206 and away from the pulleys 205 and 206.

Figure 18:
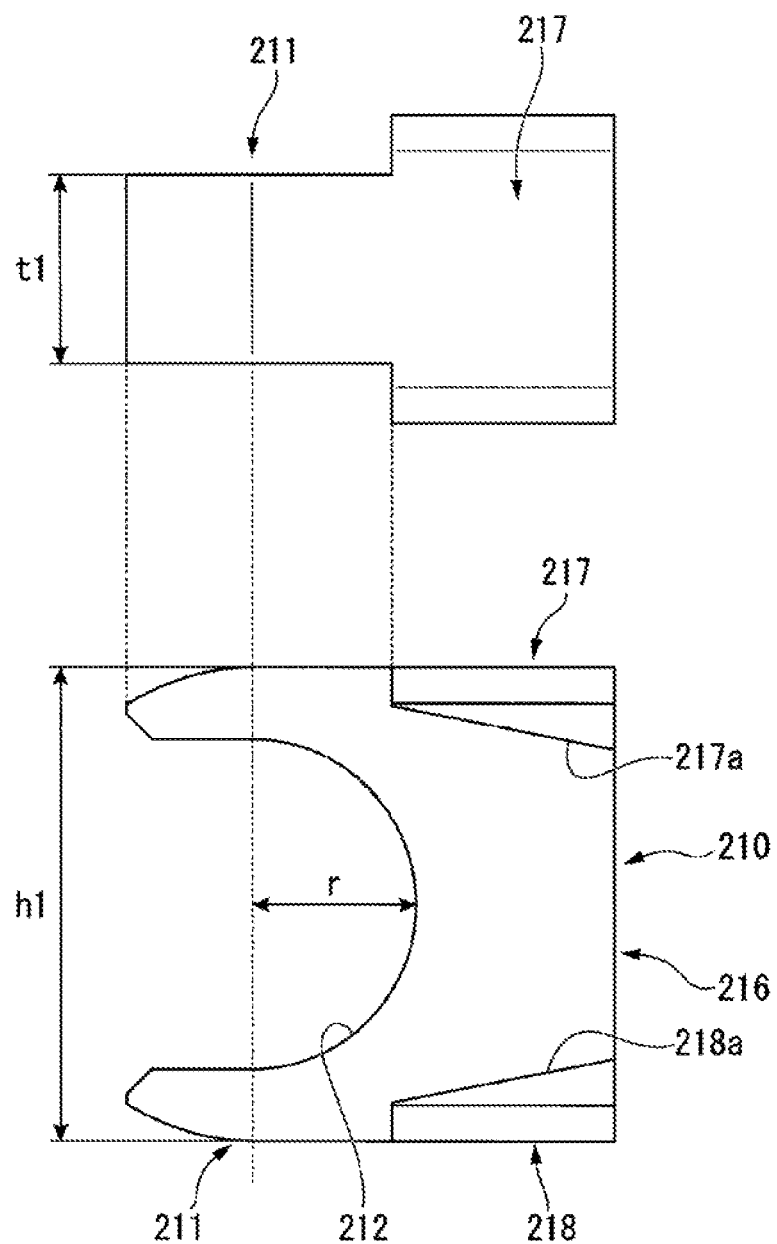
FIG. 18 depicts the spacer depicted in FIG. 17.

FIG. 18 illustrates the spacer 210. The spacer 210 includes a front side portion 211 disposed around the gear 201 and a rear side portion 216 disposed more closely to the proximal-end side than the gear 201. The front side portion 211 has a thickness t1 smaller than the distance between the pulleys 205 and 206 so that it can enter between the pulleys 205 and 206. The smaller the dimension of the thickness t1 attributes to the lower the ability of the spacer 210 to prevent the wires 207 and 208 from being dislodged off the pulleys 205 and 206. In view of this, the thickness t1 should preferably be set to such a value that no gaps of equal to or larger than the diameter of the wires 207 and 208 is formed between the front side portion 211 and the pulleys 205 and 206 when the front side portion 211 is placed between the pulleys 205 and 206. The front side portion 211 has a height h1 that may be set to such a value that the front side portion 211 sufficiently plugs the space around the gear 201. From the standpoint of making the medical instrument 1 smaller in diameter, the height h1 should preferably be set to a value that is approximately the same as the diameter of the pulleys 205 and 206. The front side portion 211 has a generally semi-circular portion 212 defined in a front end portion thereof. The semi-circular portion 212 has a radius r of curvature larger than the radius of the gear 201 including the teeth, so that the front side portion 211 does not obstruct operation of the gear 201 when placed between the pulleys 205 and 206.

According to the present embodiment, the rear side portion 216 extends rearwardly from the rear end of the front side portion while keeping the height h1 of the front side portion 211 unchanged. The rear side portion 216 has an increased thickness on both sides in the height-wise directions, resulting in wire guides (guides) 217 and 218 on the both sides in the height-wise directions. The rear side portion 216, except for the regions where the wire guides are provided, may have a thickness set to an appropriate value, but the rear side portion 216 should preferably have a thickness which is approximately the same as the thickness t1 of the front side portion 211 for the same reasons as with the front side portion 211. Since the rear side portion 216 is disposed in a position that is free of the pulleys 205 and 206, the thickness of the rear side portion 216 may be set to a value larger than the thickness t1 insofar as it avoids contact with the wires 207 and 208.

The wire guides 217 and 218 have slanted surfaces 217a and 218a on both sides in the thickness-wise directions, the slanted surfaces 217a and 218a being progressively closer to the center in the height-wise directions toward the rear end of the spacer 210. The slanted surfaces 217a and 218a are slanted at an angle which is approximately the same as the degree to which the wires extending between the pulleys and the power transmitter are displaced.

There is no restriction on materials of which the spacer 210 may be made, and the spacer 210 may be made of resin, metal, or the like. If a material has a smooth surface to minimize friction such as, for example, polyether ether ketone (PEEK) is selected as the material of the spacer 210, then the smooth surface does not cause excessive friction even when brought into contact with the pulleys, the wires, the gear, etc. and hence does not present an obstacle to the operation of the medical instrument. When the spacer 210 is placed between the pulleys 205 and 206, the front side portion 211 plugs the space which extends around the gear 201 and which is free from the gear 91. As a result, the wires 207 and 208 are unable to move in between the pulleys 205 and 206 even when they are slackened.

Furthermore, as the rear portion 216 plugs the space behind the gear 201, or more specifically rearwardly of the rotational shaft 202 and the rear ends of the pulleys 205 and 206, it limits the wires 207 and 208 that are slackened against movement along the directions in which the rotational shaft 202 extends even in positions spaced from the pulleys 205 and 206, and the phenomenon that defines as a trigger for dislodging the wires 207 and 208 off the pulleys is suppressed.

Moreover, the wire guides 217 and 218 are present in directions away from the axis X1 for the wires 207 and 208 that extend so as to be progressively closer to the axis X1 as they go away from the pulleys 205 and 206. Therefore, if a slackened wire moves in a direction away from the axis X1, it is brought into contact with the slanted surface 217a or the slanted surface 218a and prevented from moving further away from the axis X1. Therefore, the directions in which the proximal-end sides of the wires 207 and 208 extend away from the pulleys 205 and 206 are limited to a predetermined range by the wire guides 217 and 218. As a result, even if the wires are slackened, they do not excessively move in directions away from the axis X1 and are appropriately prevented from being dislodged off the pulleys.

As described above, the medical instrument 1 according to the present embodiment includes the spacer 210 for preventing the wires 207 and 208 from being dislodged off the pulleys 205 and 206 without changing the shapes and dimensions of the pulleys and the gear in the rotation transmitter 200. Therefore, the medical instrument 1 is capable of operating with high precision and is prevented from causing situations in which it is rendered inoperative.

While the embodiment of the present disclosure has been described herein, the present disclosure is not limited to the embodiment described herein, but many structural additions, omissions, replacements, and other changes may be made without departing from the scope of the disclosed technology.

Figure 19:
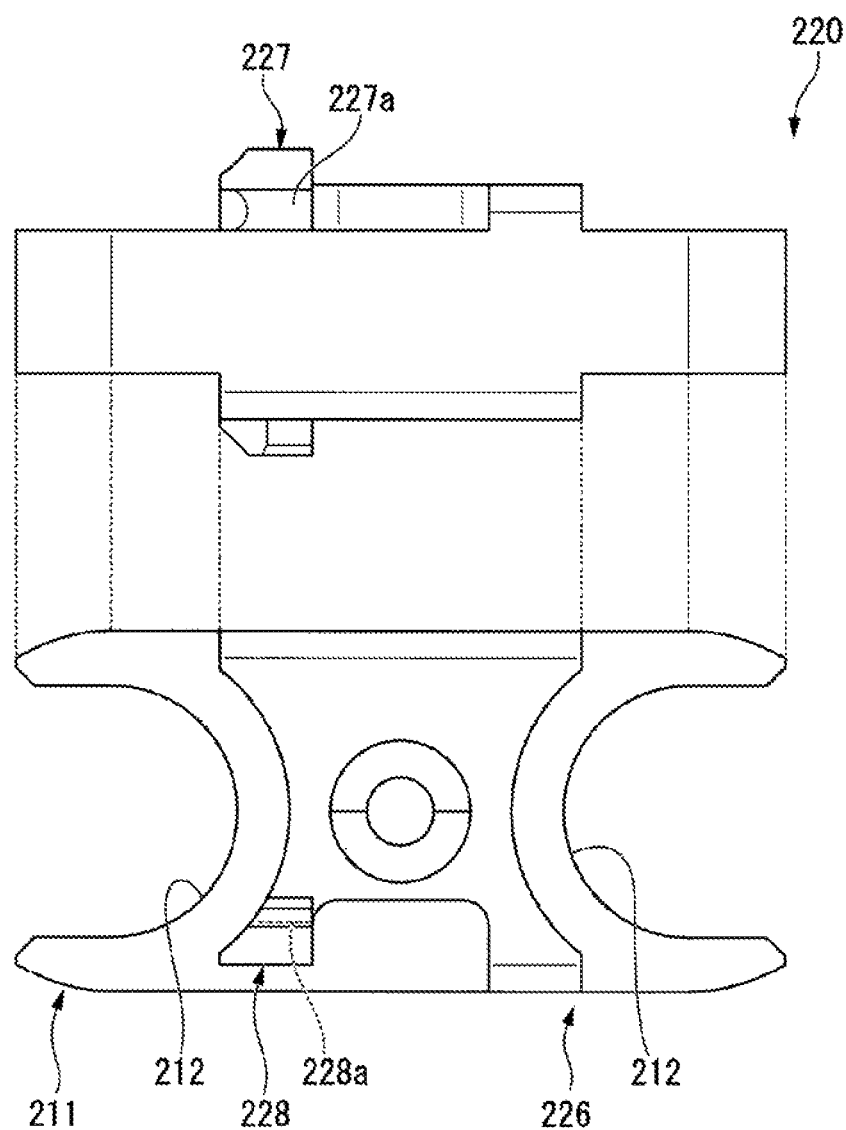
FIG. 19 depicts a modification of the spacer depicted in FIG. 17.

For example, a spacer may be disposed in other areas than the distal-end joint 90. FIG. 19 depicts a spacer 220 as an example of spacer disposed between the distal-end joint 30 and the intermediate joint 70. As with the spacer 210, the spacer 220 includes a front side portion 211 and a rear side portion 226 connected to the front side portion 211.

As with the spacer 210, the spacer 220 plugs the space around the gear 35B of the rotation transmitter 35 with the front side portion 211. The spacer 220 also includes an arcuate portion 212 provided on the rear side portion 226, so that it can enclose the space around the gear 75B of the rotation transmitter 75.

The spacer 220 also has wire guides 227 and 228 in place of the wire guides 217 and 218. In the intermediate joint, unlike the proximal-end joint, the wires extend essentially parallel to the longitudinal axis O1. Therefore, the wires 227 and 228 do not have slanted surfaces but have only guide slots 227a and 228a for preventing the wires from being displaced.

In the spacers according to the present disclosure, the wire guides are not indispensable. The spacers may be devoid of wire guides insofar as they can sufficiently plug the space around the gear.

In the medical instrument 1, since one end of a wire is attached to an outer circumferential surface of a pulley, the wire is not likely to be slackened on a side of the pulley where the end of the wire is attached in a rear side portion of the pulley along which a rear side portion of the wire extends. Therefore, the front and rear side portions of the pulley may be shaped to enclose only the space where the proximal-end side of the wire extends. In addition, the spacers according to the technology disclosed herein may not necessarily be members independent of other parts. For example, a cover housing a rotation transmitter therein and a spacer may be formed as an integral component by injection molding, cutting, or the like.

According to the present embodiment, the medical instrument 1 may define as gripping forceps with the end effector 10 including a pair of grippers 11. However, the medical instrument 1 is not limited to such an application. The end effector 10 may have another treatment tool such as a high-frequency knife or the like or may be observing means including an image capturing device or the like.

According to the present embodiment, in the distal-end joint 30, the rotation transmitter 31A and the rotation transmitter 32A are operatively connected to each other for combined angular movement by the gear 31C and the gear 32C, so that angular movement can be transmitted between the rotation transmitter 31A and the rotation transmitter 32A. However, rotation transmitters are not limited to such a structure. Angular movement may be transmitted by two tooth-free rollers held in frictional contact with one another or by wires and pulleys. Furthermore, other known methods for transferring angular movement may be employed. This also holds true for the transmission of angular movement between the rotation transmitter 34C and the rotation transmitter 35 and also for the intermediate joint 70. The elongate member 51 of the main body 50 may be made from soft or hard materials.

The target to which the spacers are applied is not limited to the medical instrument 1 of the above construction. Medical instruments that are different in structure from the medical instrument 1 may incorporate spacers that may be modified in shape and disposed for preventing wires from being dislodged off pulleys, insofar as those medical instruments have a structure in which wires are wound around rotating bodies such as pulleys or the like and there is a space in which the wires are movable along any of the directions in which the rotational shafts of the pulleys extend. For example, the spacers are applicable to an arrangement in which a single wire is wound around a single pulley and has both ends extending rearwardly of the pulley and connected to a power transmitter. The spacers are also applicable to a medical instrument that is provided with a drive mechanism which is free of gears but has only pulleys and wires.

In the medical instrument, the transmitting member may not be a wire having a circular cross-sectional shape. Rather, the transmitting member may be a wire having a rectangular cross-sectional shape, a belt having a flat cross-sectional shape, or the like.

The disclosed technology is directed to a medical instrument comprises a first pulley configured to be rotatable about a rotational shaft. A transmitting member having a first end portion and a second end portion. The first end portion is disposed along an outer circumferential surface of the first pulley and the second end portion extends tangentially to the first pulley and away from the first pulley. The transmitting member being capable of rotating the first pulley upon being actuated to move forwardly or rearwardly in longitudinal directions thereof. A dislodgement guard is disposed on at least one side of the first pulley along a direction in which the rotational shaft extends with respect to the second end portion of the transmitting member for preventing the transmitting member from being dislodged off the first pulley.

The second end portion of the transmitting member is progressively displaced along the direction in which the rotational shaft extends in a direction away from the first pulley. The medical instrument further comprises a gear having a pitch circle diameter smaller than the first pulley and is disposed coaxially with the first pulley on at least one side of the first pulley along a direction in which the rotational shaft extends with respect to the first pulley for rotation in unison with the first pulley. The dislodgement guard is disposed to plug at least a portion of a space around the gear. The medical instrument further comprises a second pulley being disposed coaxially with the first pulley and the gear being interposed between the first pulley and the second pulley. The dislodgement guard has at least a portion being disposed between the first pulley and the second pulley. The dislodgement guard has a guide for defining a direction in which a portion of the transmitting member that extends away from the first pulley extends in that direction. The first end portion of the transmitting member in the longitudinal directions thereof is attached to an outer circumferential surface of the first pulley. The dislodgement guard has at least a portion being disposed more closely to a second end portion of the transmitting member than the rotational shaft.

While various embodiments of the disclosed technology have been described above, it should be understood that they have been presented by way of example only, and not of limitation. Likewise, the various diagrams may depict an example schematic or other configuration for the disclosed technology, which is done to aid in understanding the features and functionality that can be included in the disclosed technology. The disclosed technology is not restricted to the illustrated example schematic or configurations, but the desired features can be implemented using a variety of alternative illustrations and configurations. Indeed, it will be apparent to one of skill in the art how alternative functional, logical or physical locations and configurations can be implemented to implement the desired features of the technology disclosed herein.

Although the disclosed technology is described above in terms of various exemplary embodiments and implementations, it should be understood that the various features, aspects and functionality described in one or more of the individual embodiments are not limited in their applicability to the particular embodiment with which they are described, but instead can be applied, alone or in various combinations, to one or more of the other embodiments of the disclosed technology, whether or not such embodiments are described and whether or not such features are presented as being a part of a described embodiment. Thus, the breadth and scope of the technology disclosed herein should not be limited by any of the above-described exemplary embodiments.

Terms and phrases used in this document, and variations thereof, unless otherwise expressly stated, should be construed as open ended as opposed to limiting. As examples of the foregoing: the term "including" should be read as meaning "including, without limitation" or the like; the term "example" is used to provide exemplary instances of the item in discussion, not an exhaustive or limiting list thereof; the terms "a" or "an" should be read as meaning "at least one", "one or more" or the like; and adjectives such as "conventional", "traditional", "normal", "standard", "known" and terms of similar meaning should not be construed as limiting the item described to a given time period or to an item available as of a given time, but instead should be read to encompass conventional, traditional, normal, or standard technologies that may be available or known now or at any time in the future. Likewise, where this document refers to technologies that would be apparent or known to one of ordinary skill in the art, such technologies encompass those apparent or known to the skilled artisan now or at any time in the future.

The presence of broadening words and phrases such as "one or more", "at least", "but not limited to" or other like phrases in some instances shall not be read to mean that the narrower case is intended or required in instances where such broadening phrases may be absent. Additionally, the various embodiments set forth herein are described in terms of exemplary schematics, block diagrams, and other illustrations. As will become apparent to one of ordinary skill in the art after reading this document, the illustrated embodiments and their various alternatives can be implemented without confinement to the illustrated examples. For example, block diagrams and their accompanying description should not be construed as mandating a particular configuration.

What is claimed is:

1. A medical instrument comprising:
    a first pulley configured to be rotatable about a rotational shaft;
    a transmitting member having a first end portion and a second end portion wherein the first end portion being disposed along an outer circumferential surface of the first pulley and the second end portion extends tangentially to the first pulley and away from the first pulley, the transmitting member being capable of rotating the first pulley upon being actuated to move forwardly or rearwardly in longitudinal directions thereof; and
    a dislodgement guard being disposed on at least one side of the first pulley along a direction in which the rotational shaft extends with respect to the second end portion of the transmitting member for preventing the transmitting member from being dislodged off the first pulley; and
    the medical instrument further comprising:
    a gear having a pitch circle diameter smaller than the first pulley and being disposed coaxially with the first pulley on at least one side of the first pulley along a direction in which the rotational shaft extends, with respect to the first pulley for rotation in unison with the first pulley; and
    wherein the dislodgement guard is disposed to plug at least a portion of a space around the gear; and
    a second pulley being disposed coaxially with the first pulley and the gear being interposed between the first pulley and the second pulley; wherein the dislodgement guard has at least a portion being disposed between the first pulley and the second pulley; and
    wherein the dislodgement guard has a first guide for defining a direction in which a portion of the transmitting member that extends away from the first pulley extends in that direction; and
    a second guide for defining a direction in which a portion of the transmitting member that extends away from the second pulley extends in that direction.

2. The medical instrument of claim 1, wherein the second end portion of the transmitting member is progressively displaced along the direction in which the rotational shaft extends in a direction away from the first pulley.

3. The medical instrument according to claim 1, wherein the first end portion of the transmitting member in the longitudinal directions thereof is attached to an outer circumferential surface of the first pulley.

4. The medical instrument according to claim 3, wherein the dislodgement guard has at least a portion being disposed more closely to a second end portion of the transmitting member than the rotational shaft.

* * * * *